(12) United States Patent
Reuter et al.

(10) Patent No.: US 6,641,871 B2
(45) Date of Patent: Nov. 4, 2003

(54) LIQUID-CRYSTAL COMPOUND, LIQUID-CRYSTAL MEDIUM COMPRISING SAME, AND ELECTRO-OPTICAL LIQUID-CRYSTAL DISPLAY

(75) Inventors: Marcus Reuter, Darmstadt (DE); Michael Heckmeier, Bensheim (DE); Volker Reiffenrath, Rossdorf (DE)

(73) Assignee: Merck Patent Gesellschaft mit, Darmstadt (DE)

( * ) Notice: Subject to any disclaimer, the term of this patent is extended or adjusted under 35 U.S.C. 154(b) by 66 days.

(21) Appl. No.: 09/960,723

(22) Filed: Sep. 24, 2001

(65) Prior Publication Data
US 2003/0006399 A1 Jan. 9, 2003

(30) Foreign Application Priority Data

Sep. 22, 2000 (DE) .......................................... 100 47 059

(51) Int. Cl.⁷ ........................ C09K 19/30; C09K 19/12; C09K 19/34; C07C 49/533
(52) U.S. Cl. .............. 428/1.1; 252/299.65; 252/299.66; 252/299.61; 568/381
(58) Field of Search ...................... 568/381; 252/299.63, 252/299.66, 299.61; 349/144; 428/1.1

(56) References Cited

U.S. PATENT DOCUMENTS 5,495,355 A * 2/1996 Konuma et al. .............. 359/78
5,545,747 A * 8/1996 Kawaguchi et al. ......... 560/123
5,748,275 A * 5/1998 Sato et al. ................... 349/144

FOREIGN PATENT DOCUMENTS

| DE | 4206771 | * | 9/1992 |
| DE | 19955932 | * | 5/2000 |
| JP | 5-78320 | * | 3/1993 |

* cited by examiner

Primary Examiner—Shean C. Wu
(74) Attorney, Agent, or Firm—Millen, White, Zelano & Branigan, P.C.

(57) ABSTRACT

The present invention relates to compounds containing a cyclobutanone group of the formula I

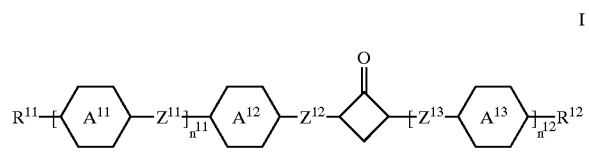

where the various parameters are as defined in the text, and to liquid-crystal media which comprise these compounds, and to their use in electro-optical displays, in particular in PA LCDs.

15 Claims, No Drawings

LIQUID-CRYSTAL COMPOUND, LIQUID-CRYSTAL MEDIUM COMPRISING SAME, AND ELECTRO-OPTICAL LIQUID-CRYSTAL DISPLAY

The present invention relates to mesogenic compounds, in particular liquid-crystalline compounds, and to liquid-crystalline media comprising these compounds. The present invention furthermore relates to liquid-crystal displays, in particular liquid-crystal displays addressed by means of an active matrix (AMDs or AM LCDs (active matrix addressed liquid crystal displays) and very particularly so-called plasma-addressed liquid-crystal displays (PA LCDs), in which the active electrically nonlinear medium is the plasma in the plasma channels.

In liquid-crystal displays of this type, the liquid crystals are used as dielectrics whose optical properties change reversibly on application of an electric voltage. Electro-optical displays which use liquid crystals as media are known to the person skilled in the art. These liquid-crystal displays use various electro-optical effects. The most common of these are the TN effect (twisted nematic, with a homogeneous, virtually planar initial alignment of the liquid crystals and a nematic structure twisted by about 90°), the STN effect (supertwisted nematic) and the SBE effect (supertwisted birefringence effect). In these and similar electro-optical effects, liquid-crystalline media of positive dielectric anisotropy ($\epsilon$B) are used.

Besides the said electro-optical effects, which require liquid-crystal media of positive dielectric anisotropy, there are other electro-optical effects which use liquid-crystal media of negative dielectric anisotropy, such as, for example, the ECB effect (electrically controlled birefringence) and its sub-forms DAP (deformation of aligned chases), VAN (vertically aligned nematics) and CSH (color super homeotropics).

An electro-optical effect having excellent, low, viewing-angle dependence of the contrast uses axially symmetric micropixels (ASMs). In this effect, the liquid crystal in each pixel is surrounded cylindrically by a polymer material. This mode is particularly suitable for combination with addressing through plasma channels. Thus, in particular, large-area PA LCDs having good viewing-angle dependence of the contrast can be achieved.

The IPS effect (in plane switching), which has been increasingly employed recently, can use both dielectrically positive and dielectrically negative liquid-crystal media, similar to guest/host displays, which are able to employ dyes either in dielectrically positive or in dielectrically negative media, depending on the display mode used.

Since the operating voltage in displays should generally, i.e. including in displays based on these effects, be as low as possible, use is made of liquid-crystal media of large dielectric anisotropy, which generally predominantly and usually even very substantially consist of liquid-crystal compounds of the corresponding dielectric anisotropy, i.e. consist of compounds of positive dielectric anisotropy in the case of dielectrically positive media and of compounds of negative dielectric anisotropy in the case of dielectrically negative media. In the respective types of media (dielectrically positive or dielectrically negative), at most significant amounts of dielectrically neutral liquid-crystal compounds are typically employed. Liquid-crystal compounds having the sign of the dielectric anisotropy opposite to the dielectric anisotropy of the medium are generally employed in extremely small amounts, or not at all.

An exception here is formed by liquid-crystalline media for MIM (metal-insulator-metal) displays [J. G. Simmons, Phys. Rev. Vol 155 No. 3, pp. 657–660; K. Niwa et al., SID 84 Digest, pp. 304–307, June 1984], in which the liquid-crystal media are addressed by means of an active matrix of thin-film transistors. In this type of addressing, which utilizes the non-linear characteristic line of diode switching, it is not possible, in contrast to TFT displays, to charge a storage capacitor together with the electrodes of the liquid-crystal display elements (pixels). A reduction in the effect of voltage drop during the addressing cycle therefore requires the highest possible base value of the dielectric constant. In dielectrically positive media, as employed, for example, in MIM-TN displays, the dielectric constant perpendicular to the molecular axis ($\epsilon_\perp$) must therefore be as large as possible, since it determines the base capacitance of the pixel. To this end, as in WO 93/01253, EP 0 663 502 and DE 195 21 483, compounds of negative dielectric anisotropy are employed in addition to dielectrically positive compounds in the dielectrically positive liquid-crystal media.

A further exception is formed by STN displays in which, for example in accordance with DE 41 00 287, dielectrically positive liquid-crystal media comprising dielectrically negative liquid-crystal compounds are employed in order to increase the steepness of the electro-optical characteristic line.

The pixels of the liquid-crystal displays can be addressed directly, time-sequentially, i.e. in time multiplex mode, or by means of a matrix of active, electrically nonlinear elements.

The most common AMDs to date use discrete active electronic switching elements, such as, for example, three-pole switching elements, such as MOS (metal oxide silicon) transistors or thin-film transistors (TFTs) or varistors or 2-pole switching elements, such as, for example, MIM (metal insulator metal) diodes, ring diodes or back-to-back diodes. In TFTs, various semiconductor materials, predominantly silicone or alternatively cadmium selenide, are used. In particular, amorphous silicon or polycrystalline silicon is used.

In contrast to these conventional AMDs, the electrically nonlinear material in PA LCDs is not a solid semiconductor material, but instead a gaseous plasma. This plasma is located in discharge chambers which have the shape of channels. These channels run parallel to one another and thus define the rows (or columns) of the matrix. The signal electrodes, to which the addressing voltages for all pixels of a row (or column) are applied parallel to one another, run perpendicular to the plasma channels.

The plasma in PA LCDs is separated from the liquid-crystal layer by a thin insulating layer, known as the microsheet. As in conventional AMDs, the alignment layer is located on this microsheet in a conventional manner.

In contrast to conventional AMDs, however, voltage additionally drops over the microsheet in PA LCDs. This drop in voltage is generally significant, which means that the plasma voltage ($V_{plasma}$) is divided as follows into the voltage drop over the liquid-crystal layer ($V_{LC}$) and over the microsheet ($V_{sheet}$):

$$V_{plasma} = V_{LC} + V_{sheet} \quad (I)$$

Taking into account the capacitance of the liquid-crystal layer ($C_{LC}$) and of the microsheet ($C_{sheet}$), which are determined by the respective layer thicknesses ($d_{LC}$ and $d_{sheet}$ respectively) and dielectric constants ($\epsilon_{LC}$ and $\epsilon_{sheet}$ respectively) since the active surfaces of the two layers correspond, the following is obtained:

$$V_{plasma}/V_{LC} = 1 + (\epsilon_{LC}/d_{LC}) \cdot (d_{sheet}/\epsilon_{sheet}) \quad (II)$$

The effective dielectric constant of the liquid-crystal layer ($\epsilon E_{LC,eff}$) is not constant, but instead depends on the applied voltage and the material properties of the liquid-crystal material, and on the initial alignment and the electrode configuration. It is always in the region of the two extreme values, namely the dielectric constants perpendicular to the director (to a first approximation the longitudinal molecular axis) ($\epsilon_\perp$) and the dielectric constant parallel to the director ($\epsilon_\parallel$).

In displays having an electric field perpendicular to the liquid-crystal layer and liquid-crystal media of negative dielectric anisotropy ($\Delta\epsilon<0$) and a homeotropic edge alignment, which are preferred for the purposes of the present application, the liquid-crystal director in the fully switched-through state, i.e. on application of a correspondingly large voltage, is aligned parallel to the layer plane, and the effective dielectric constant is the dielectric constant perpendicular to the director ($\epsilon_{\perp=\epsilon LC,eff}$). The ratio of the voltages is thus as follows:

$$V_{plasma,sat.}/V_{LC,on}=1+(\epsilon_\perp/d_{LC})\cdot(d_{sheet}/\epsilon_{sheet}) \quad (III)$$

The smallest possible value of $\epsilon_\perp$ is thus desired for PA LCDs.

However, this requirement is contrary to the fact that, in particular, the threshold voltage, but also the saturation voltage of the electro-optical effect is dependent on the dielectric anisotropy and to a first approximation is inversely proportional thereto, i.e. increases at low values of $\epsilon_\perp$, which is undesired. This is evident if the plasma voltage is written as a function of the dielectric constants:

$$V_{plasma,sat.}=V_{LC,on}[1+(\epsilon_\perp/d_{LC})\cdot(d_{sheet}/\epsilon_{sheet})] \quad (IV)$$

and $$V_{LC,on}\cong(\text{const.}/\Delta\epsilon)^{1/2}=(\text{const.}/(\epsilon_\perp-\epsilon_\parallel))^{1/2};\ V_{plasma,sat.}=\text{const.}(1/(\epsilon_\perp-\epsilon_\parallel))^{1/2}+\epsilon_\perp/(\epsilon_\perp-\epsilon_\parallel))^{1/2}\cdot d_{sheet}/(d_{LC}\cdot\epsilon_{sheet})) \quad (V)$$

The plasma voltage curve given by equation (V) for the saturation state as a function of the dielectric constant perpendicular to the director can be described qualitatively as follows for a typical PA LCD containing a customary liquid-crystal medium. The plasma voltage for the saturation state initially drops to a relatively great extent with increasing dielectric constant perpendicular to the director. However, the drop becomes less and less, and $V_{plasma,sat.}$ passes through a minimum at an $\epsilon_\perp$ value which is typically in the range from about 5 to 6. Then, i.e. at larger $\epsilon_\perp$ values, $V_{plasma,sat.}$ increases again. The rise is less steep than the drop before the minimum, but increases significantly with increasing $\epsilon_\perp$, at least initially.

In formula (V), the second liquid-crystal material parameter besides $\epsilon_\perp$ is $\epsilon_\parallel$. If the $V_{plasma,sat.}(\epsilon_\perp)$ as a function of $\epsilon_\parallel$ is considered, it can be seen that smaller values of $\epsilon_\parallel$ shift the curves to smaller voltage values, i.e. result in more favourable, lower addressing voltages.

Ketones of the formula

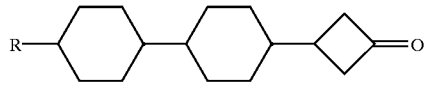

have been disclosed by E. Poetsch et al.; 14$^{th}$ Internat. Liquid Crystal Conference, Jun. 21–26, 1992, Pisa, Poster Section A, and 15$^{th}$ Internat. Liquid Crystal Conference, Jul. 03–08, 1994, Lecture Series B. They have low optical anisotropy, but are dielectrically positive.

Ketones, for example of the formula

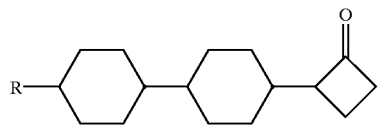

have been disclosed in DE 199 55 932. However, no liquid-crystal mixtures are disclosed therein.

It can thus be seen that there is both a demand for further mesogenic compounds and a demand for liquid-crystal media, in particular of negative dielectric anisotropy and low $\epsilon_\perp$.

Since this requirement is extremely difficult to achieve, or cannot be achieved at all, with conventional materials, even the satisfying of the usual criteria for media of this type, such as broad nematic phase range, correct value of the optical anisotropy ($\Delta n$) and low viscosity, while also important, is generally to be regarded as secondary. There thus was and is a great demand for liquid-crystal media which do not have the disadvantages of the prior-art media or at least do so to a significantly reduced extent, and which, in particular, have a low value of $\epsilon_\perp$.

This is achieved by the use of the liquid-crystal compounds of the formula I according to the invention, which have a low value of $\epsilon_\perp$,

I

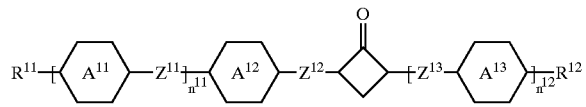

in which $R^{11}$ and $R^{12}$ are each, independently of one another, H, an alkyl group having 1 to 15 carbon atoms which is monosubstituted by CN or CF$_3$ or at least monosubstituted by halogen, and in which, in addition, one or more CH$_2$ groups, in each case independently of one another, may be replaced by —O—, —S—, —CH=CH—,

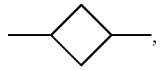

—C≡C—, —CO—O—, —O—CO— or —O—CO—O— in such a way that O atoms are not linked directly to one another, and $R^{11}$ and $R_{12}$ are preferably alkyl or alkoxy having 1 to 12 carbon atoms or alkoxyalkyl, alkenyl or alkenyloxy having 2 to 12 carbon atoms, $Z^{11}$, $Z^{12}$ and $Z^{13}$ are each, independently of one another, —CH$_2$—CH$_2$—, —CH=CH—, —C≡C—, —COO—, —OCO—, —CH$_2$O—, —OCH$_2$—, —CF$_2$O—, —OCF$_2$—, —(CH$_2$)$_4$—, —CF=CF—, —CH=CF—, —CF=CH— or a single bond, preferably —CH$_2$—CH$_2$—, —CH=CH—, —C≡C—, —COO— or a single bond, particularly preferably —CH$_2$—CH$_2$— or a single bond,

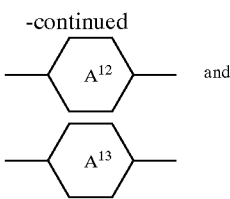

are each, independently of one another,
(a) a trans-1,4-cyclohexylene radical, in which, in addition, one or two non-adjacent CH$_2$ groups may independently be replaced by —O— or —S—,
(b) a 1,4-cyclohexenylene radical,
(c) a 1,4-phenylene radical, in which, in addition, one or two CH groups may be replaced by N, or
(d) a radical selected from the group consisting of 1,4-bicyclo-[2.2.2]octylene, piperidine-1,4-diyl, naphthalene-2,6-diyl, decahydronaphthalene-2,6-diyl and 1,2,3,4-tetrahydronaph-thalene-2,6-diyl, whereby in any of the rings (a) to (d) one, two or more hydrogen atoms bound to a carbon atom may be replaced by a fluorine atom,
and rings (a) to (d) are
preferably, in each case independently of one another,

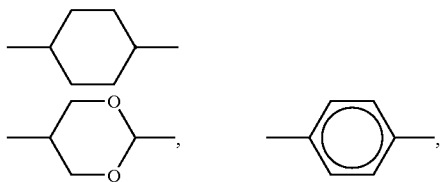

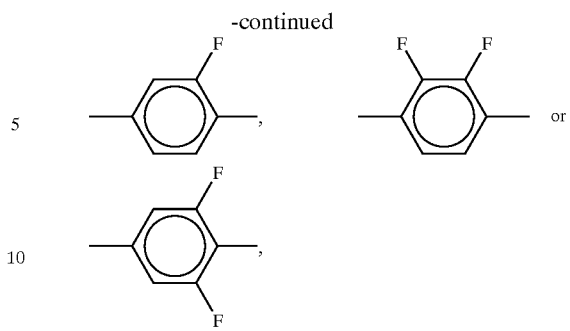

and $n^{11}$ and $n^{12}$ are each 0, 1 or 2, where $n^{11}+n^{12}$ is 1, 2 or 3, preferably 2 or 3.

Compounds of the formula I in which $Z^{12}$ is not a single bond, or $n^{12}$ is 1 or 2, or both $Z^{12}$ is not a single bond and $n^{12}$ is 1 or 2, and in the case where $n^{11}$ is 0, $Z^{13}$ is not a single bond are novel and are preferred subject-matter of the present application.

Compounds of the formula I containing branched wing groups $R^{11}$ and/or $R^{12}$ may occasionally be of importance owing to better solubility in the conventional liquid-crystalline base materials, but in particular as chiral dopants if they are optically active. Smectic compounds of this type are suitable as components of ferroelectric materials.

Compounds of the formula I having $S_A$ phases are suitable, for example, for thermally addressed displays.

Particular preference is given to liquid-crystal compounds of the sub-formulae I1 to I21:

I1
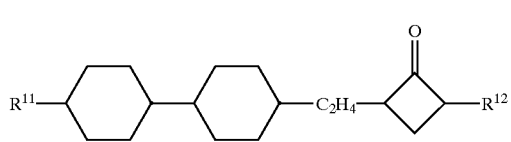

I2
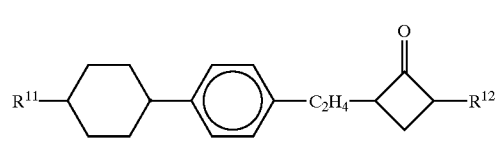

I3
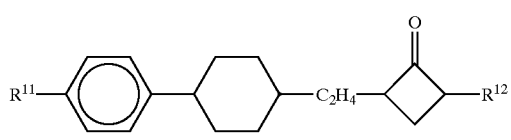

I4
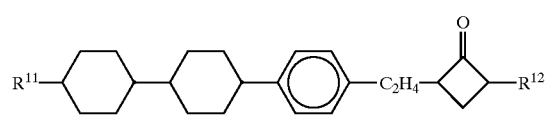

I5
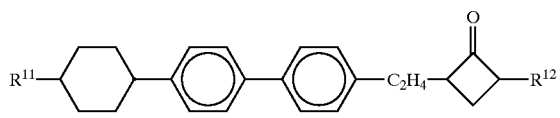

I6
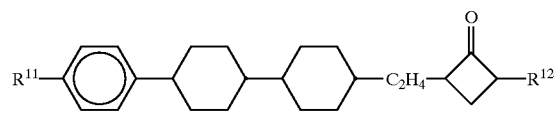

I7
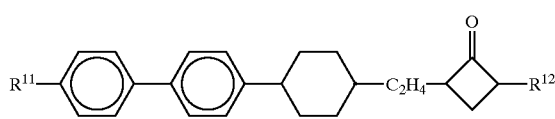

I8
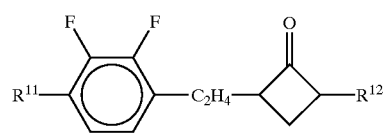

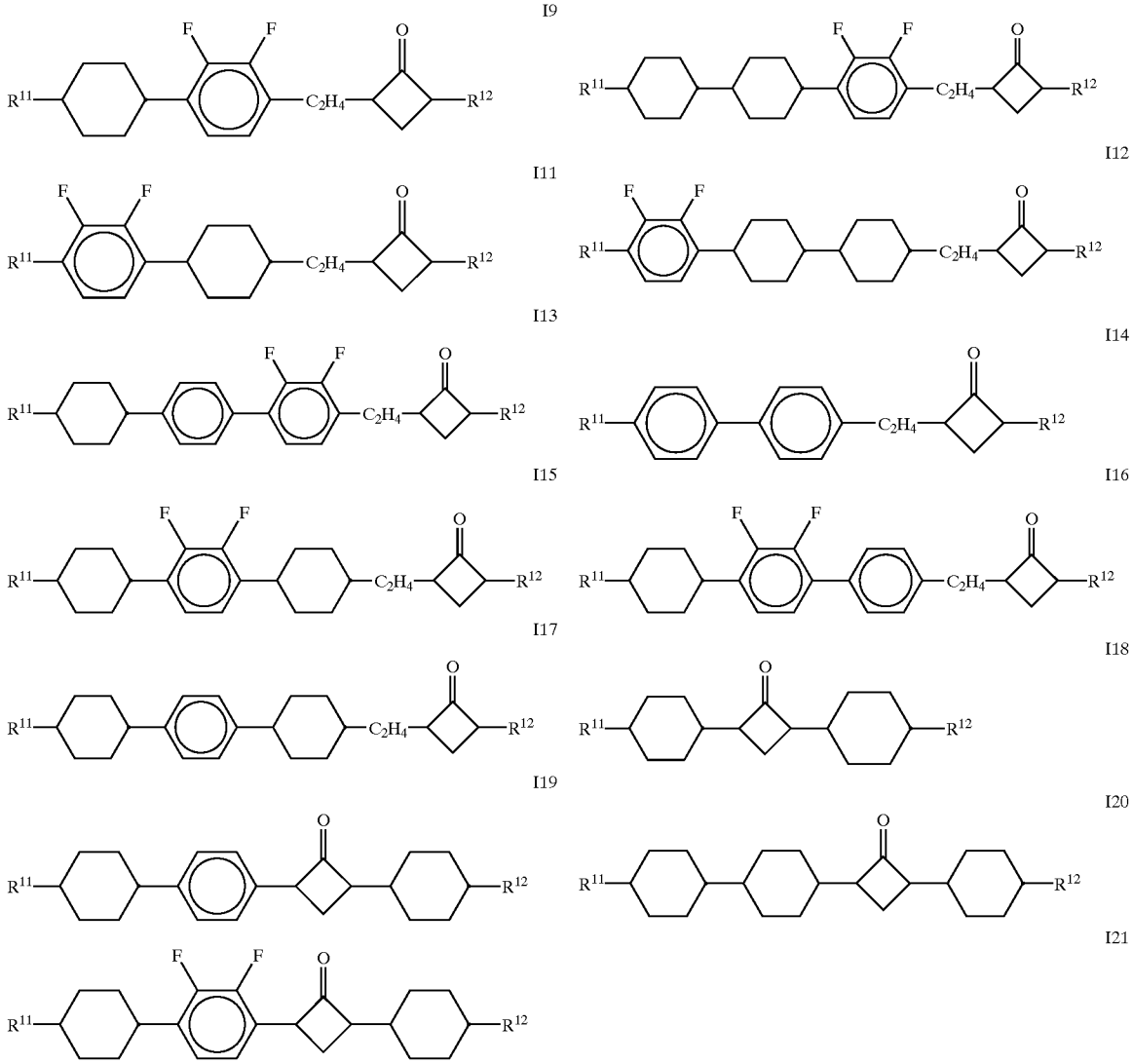

in which

R[11] and R[12] are as defined above under the formula I.

If R[11] and/or R[12] is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl or alkoxyalkyl is preferably straight-chain 2-oxapropyl (=methoxy-methyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-6- or 7-oxaoctyl, 2-, 3-,4-, 5-, 6-, 7- or 8-oxanonyl, or 2-, 3-, 4-, 5-, 6-, 7-, 8- or 9-oxadecyl.

If R[11] and/or R[12] is an alkyl radical in which one CH$_2$ group has been replaced by —CH=CH—, this may be straight-chain or branched. It is preferably straight-chain and has 2 to 10 carbon atoms. Accordingly, it is in particular vinyl, prop-1- or prop-2-enyl, but-1-, -2- or -3-enyl, pent-1-, -2-, -3- or -4-enyl, hex-1-, -2-, -3-, 4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R[11] and/or R[12] is an alkyl radical in which one CH$_2$ group has been replaced by —O— and one has been replaced by —CO—, these are preferably adjacent. These thus contain an acyloxy group —CO—O— or an oxycarbonyl group —O—CO. These are preferably straight-chain and have 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)-propyl, 3-(ethoxycarbonyl)propyl or 4-(methoxycarbonyl)butyl.

If $R^{11}$ and/or $R^{12}$ is an alkyl radical in which one $CH_2$ group has been replaced by unsubstituted or substituted —CH=CH— and an adjacent $CH_2$ group has been replaced by CO or CO—O or O—CO, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxy-hexyl, 7-acryloyloxyheptyl, 8-acryloyloxyoctyl, 9-acryloyloxynonyl, 10-acryl-oyloxydecyl, methacryoyloxymethyl, 2-methacryloyloxyethyl, 3-methacryl-oyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If $R^{11}$ and/or $R^{12}$ is an alkyl or alkenyl radical which is monosubstituted by CN or $CF_3$, this radical is preferably straight-chain. The substitution by CN or $CF_3$ is in any desired position.

If $R^{11}$ and/or $R^{12}$ is an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Branched groups of this type preferably contain not more than one chain branch. Preferred branched radicals $R^1$ are isopropyl, 2-butyl (=1-methyl-propyl), isobutyl (=2-methylpropyl), 2-methylbutyl, isopentyl (=3-methyl-butyl), 2-methylpentyl, 3-methylpentyl, 2-ethylhexyl, 2-propylpentyl, isopropoxy, 2-methylpropoxy, 2-methylbutoxy, 3-methylbutoxy, 2-methyl-pentoxy, 3-methylpentoxy, 2-ethylhexyloxy, 1-methylhexyloxy and 1-methylheptyloxy.

If $R^{11}$ and/or $R^{12}$ is an alkyl radical in which two or more $CH_2$ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Particular preference is given to compounds of the formula I in which $n^{11}=1$ and $n^{12}=0$ and $R^{11}$ is methyl, ethyl, propyl, butyl, pentyl, vinyl, 1E-propenyl, 1E-butenyl or 1E-pentenyl, and to the media comprising these compounds. Of these compounds, the alkyl compounds are particularly preferably employed.

The term "alkyl" preferably covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" preferably covers straight-chain and branched alkenyl groups having 2–7 carbon atoms, in particular the straight-chain groups. Particularly preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of further preferred alkenyl groups are vinyl, 1 E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxyalkyl" preferably covers straight-chain radicals of the formula $C_nH_{2n+1}$—O—$(CH_2)_m$, in which n and m are each, independently of one another, from 1 to 6. n is preferably =1 and m is preferably from 1 to 6.

The compounds of the formula I are prepared in accordance with schemes I to III.

Scheme I

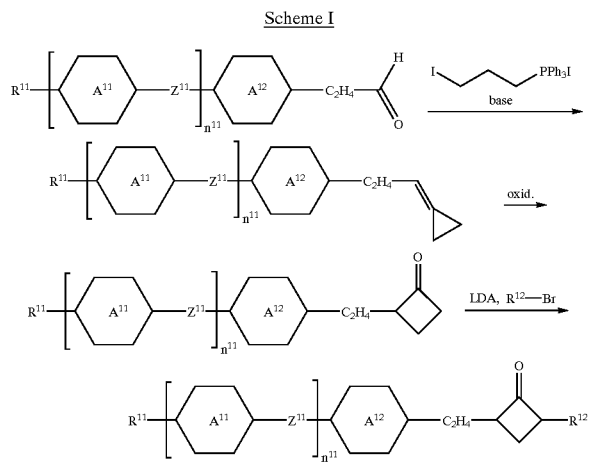

in which the parameters are as defined above under the formula I.

Scheme II

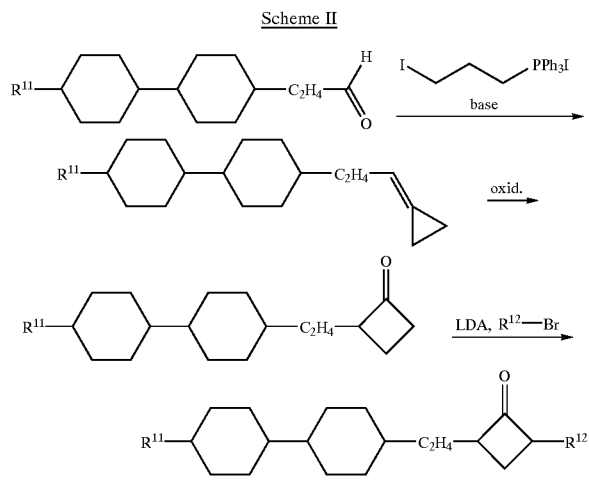

in which the parameters are as defined above under the formula I.

Scheme III

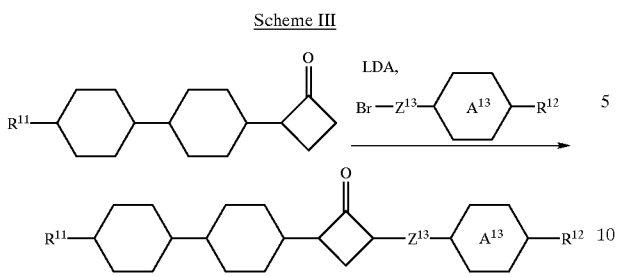

in which the parameters are as defined above under the formula I.

The liquid-crystal media according to the invention comprise one or more compounds of the formula I.

In a preferred embodiment, the liquid-crystal media in accordance with the present invention comprise a) one or more dielectrically negative compound(s) of the formula (I)

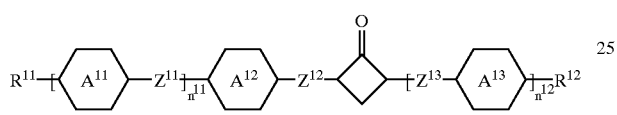

I in which $R^{11}$ and $R^{12}$ are each, independently of one another, H, an alkyl group having 1 to 15 carbon atoms which is monosubstituted by CN or $CF_3$ or at least monosubstituted by halogen, and in which, in addition, one or more $CH_2$ groups, in each case independently of one another, may be replaced by —O—, —S—, —CH=CH—,

—CO—, —CO—O—, —O—CO— or —O—CO—O— in such a way that O atoms are not linked directly to one another, preferably alkyl or alkoxy having 1 to 12 carbon atoms or alkoxyalkyl, alkenyl or alkenyloxy having 2 to 12 carbon atoms, $Z^{11}$, $Z^{12}$ and $Z^{13}$ are each, independently of one another, —$CH_2$—$CH_2$—, —CH=CH—, —C≡C—, —COO—, —OCO—, —$CH_2$O—, —O$CH_2$—, —$CF_2$O—, —O$CF_2$—, —($CH_2$)$_4$—, —CF=CF—, —CH=CF—, —CF=CH— or a single bond, preferably —$CH_2$—$CH_2$—, —CH=CH—, —C—C—, —COO— or a single bond, particularly preferably —$CH_2$—$CH_2$— or a single bond,

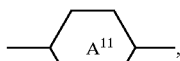

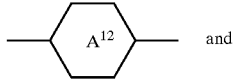

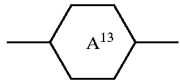

are each, independently of one another, (e) a trans-1,4-cyclohexylene radical, in which, in addition, one or more non-adjacent $CH_2$ groups may be replaced by —O— and/or —S—, (f) a 1,4-cyclohexenylene radical, (g) a 1,4-phenylene radical, in which, in addition, one or two CH groups may be replaced by N, or (h) a radical selected from the group consisting of 1,4-bicyclo-[2.2.2]octylene, piperidine-1,4-diyl, naphtalene-2,6-diyl, decahydronaphthalene-2,6-diyl and 1,2,3,4-tetrahydronaphthalene-2,6-diyl, whereby in any of the rings (e) to (h) one, two or more hydrogen atoms bound to a carbon atom may be replaced by a fluorine atom, preferably, in each case independently of one another,

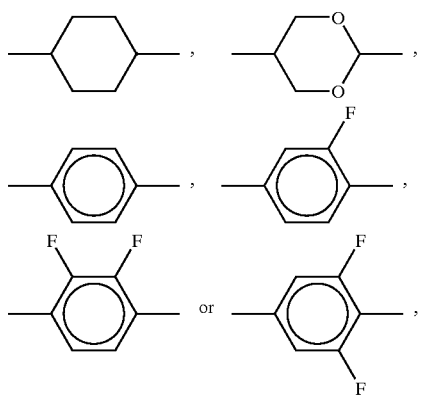

and $n^{11}$ and $n^{12}$ are each 0, 1 or 2, where $n^{11}+n^{12}$ is 1, 2 or 3, preferably 2 or 3;

b) one or more dielectrically negative compound(s) of the formula II

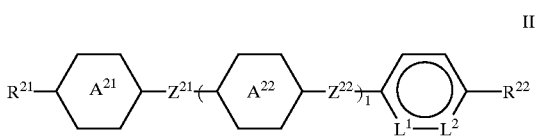

II in which $R^{21}$ and $R^{22}$ each, independently of one another, are as defined above for $R^{11}$ under the formula I, $Z^{21}$ and $Z^{22}$ each, independently of one another, are as defined above for $Z^{11}$ under the formula I,

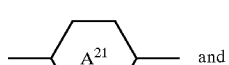
and

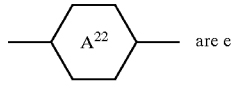
are each, independently of one another,

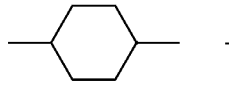

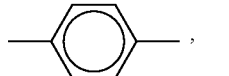

-continued

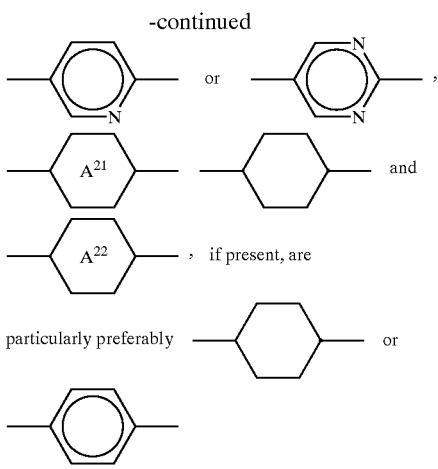

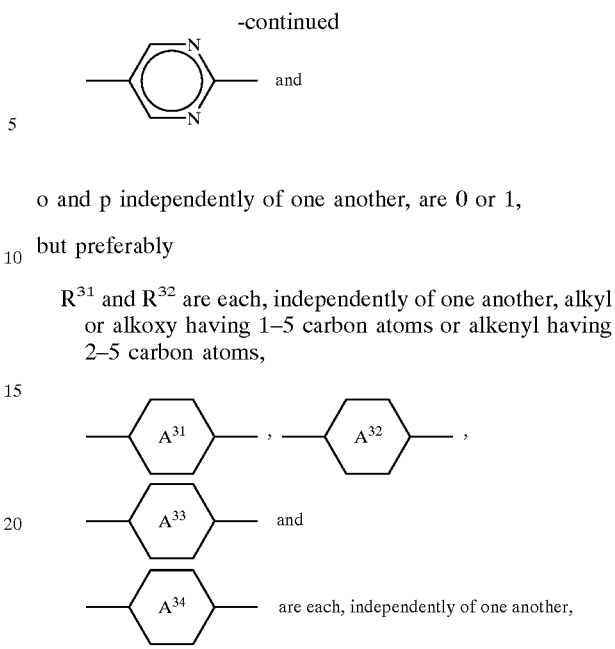

$L^1$ and $L^2$ are both C—F or one of the two is N and the other is C—F, preferably both are C—F, and l is 0 or 1;

and optionally c) one or more dielectrically neutral compound(s) of the formula III

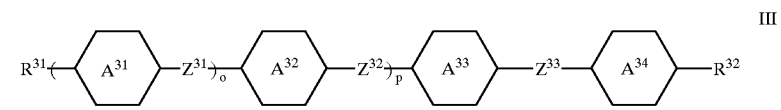

III in which $R^{31}$ and $R^{32}$ each, independently of one another, are as defined above for $R^{11}$ under the formula I, and $Z^{31}$, $Z^{32}$ and $Z^{33}$ are each, independently of one another, —CH$_2$CH$_2$—, —CH=CH—, —COO— or a single bond,

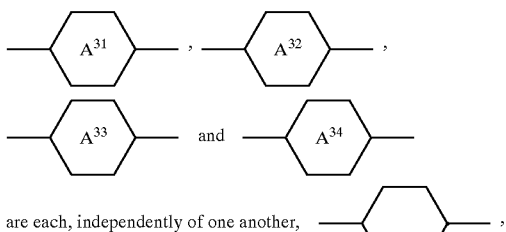

are each, independently of one another,

-continued

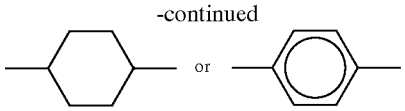

and very particularly preferably at least two of these rings are

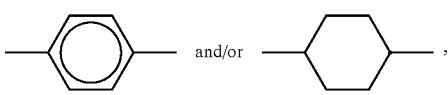

where two adjacent rings are very particularly preferably linked directly and are preferably

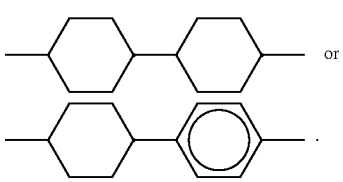

The liquid-crystal media preferably comprise one or more compounds of the formula I which contain no biphenyl unit.

The liquid-crystal media particularly preferably comprise one or more compounds of the formula I in which two adjacent rings are linked directly and are preferably

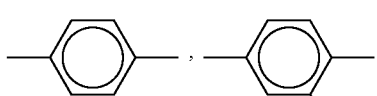

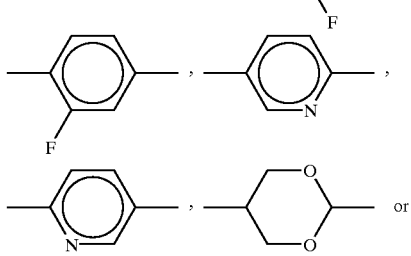

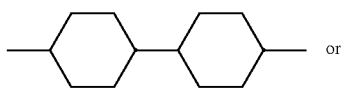 or 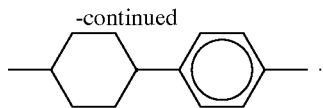
In a preferred embodiment, which may be identical with the embodiments just described, the liquid-crystal media comprise one or more compounds selected from the group consisting of the compounds of the formulae I1 to I38:
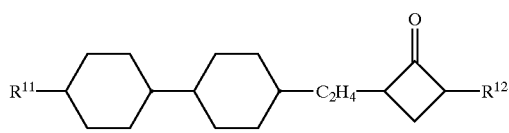 I1
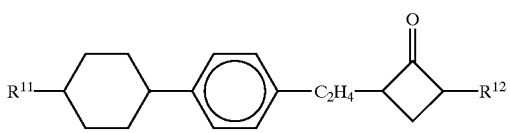 I2
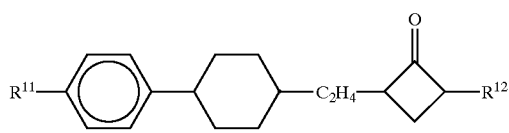 I3
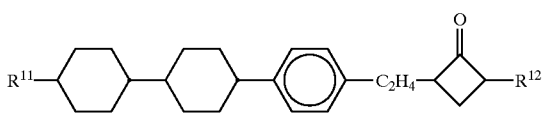 I4
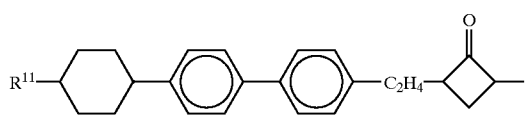 I5
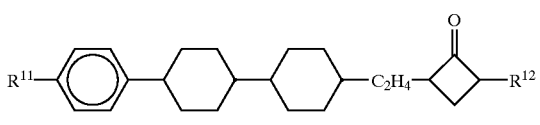 I6
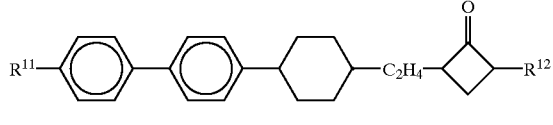 I7
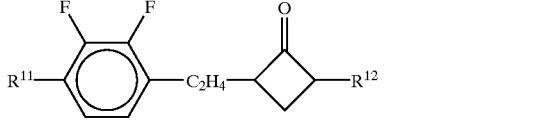 I8
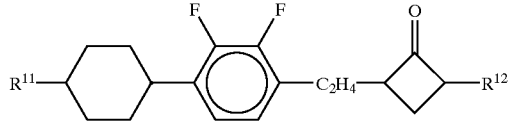 I9
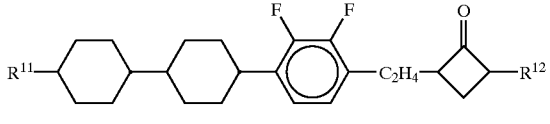 I10
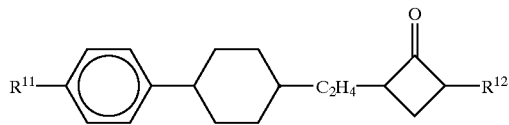 I11
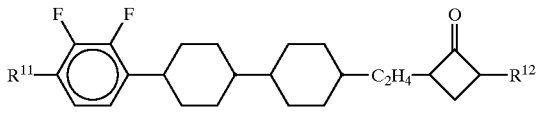 I12
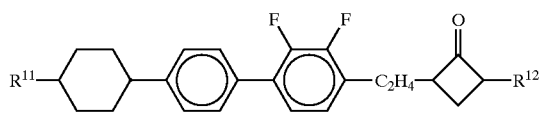 I13
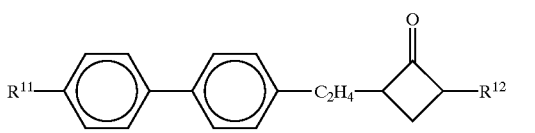 I14
 I15
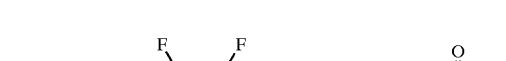 I16
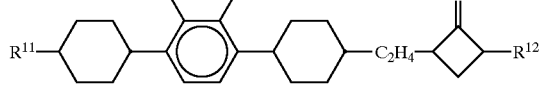 I17
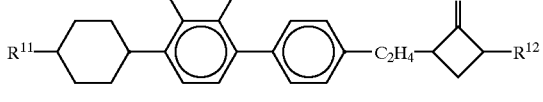 I18
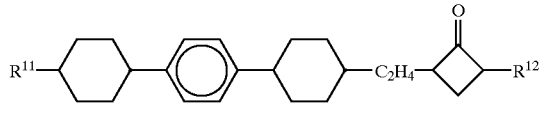

-continued
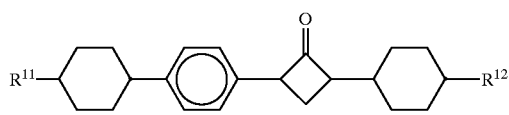 I19
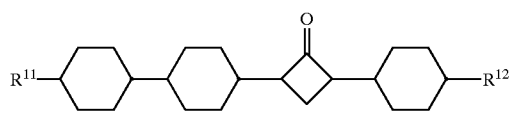 I20
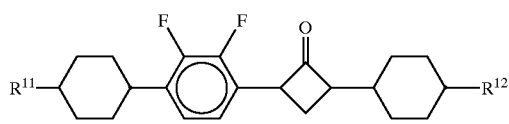 I21
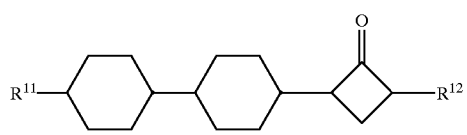 I22
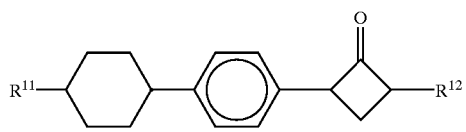 I23
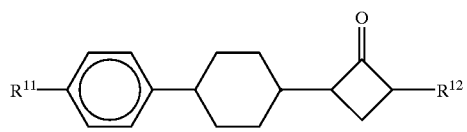 I24
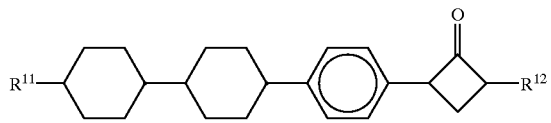 I25
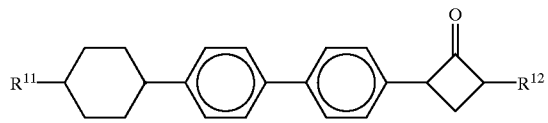 I26
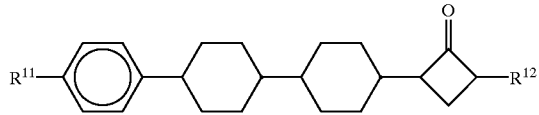 I27
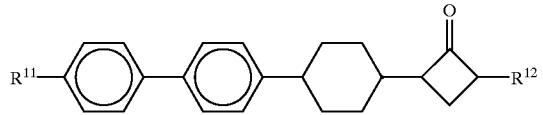 I28
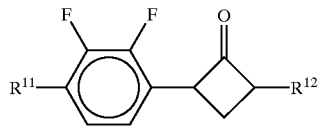 I29
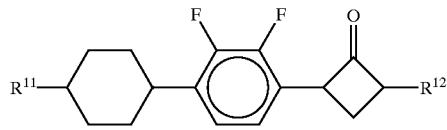 I30
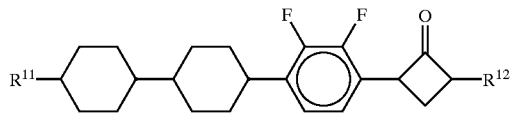 I31
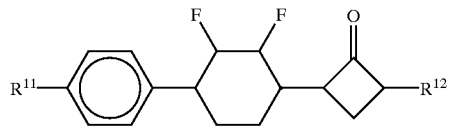 I32
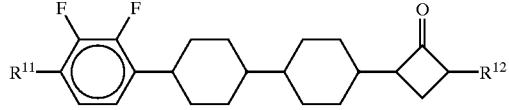 I33
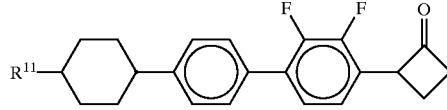 I34
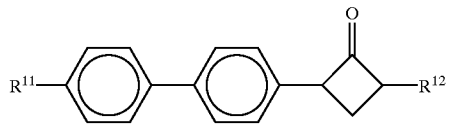 I35
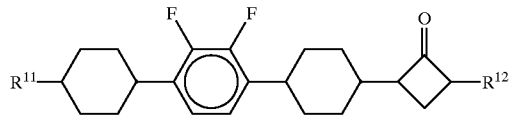 I36
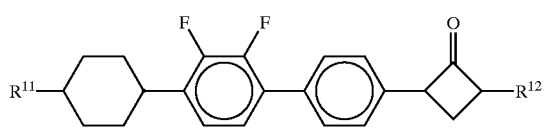 I37
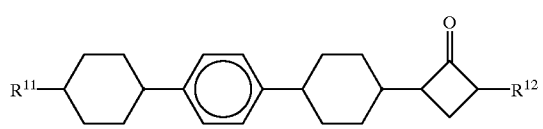 I38 in which $R^{11}$ and $R^{12}$ are as defined above under the formula I.

Of these, particular preference is given to compounds selected from the group consisting of the formulae I1 to I4, I6, I9 to I12, I15 and I17 to I21 and I22 to I25, I27, I30 and I38.

The liquid-crystal medium preferably comprises one or more compounds of the formula II1

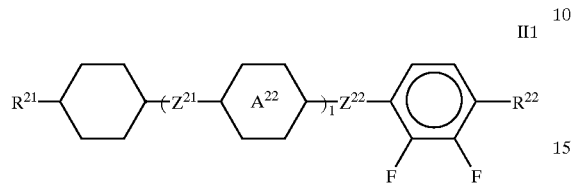

II1 in which $R^{21}$, $R^{22}$, $Z^{21}$, $Z^{22}$,

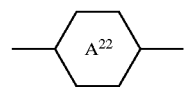

and I are each as defined above under the formula II. $R^{21}$ is preferably alkyl having 1–5 carbon atoms, $R^{22}$ is preferably alkyl or alkoxy, each having 1 to 5 carbon atoms, and $Z^{22}$ and $Z^{21}$, if present, are a single bond.

The liquid-crystal media particularly preferably comprise one or more compounds selected from the group consisting of the compounds of the formulae II1a to II1e:

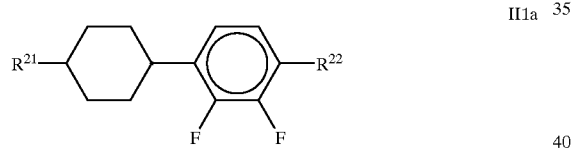

II1a

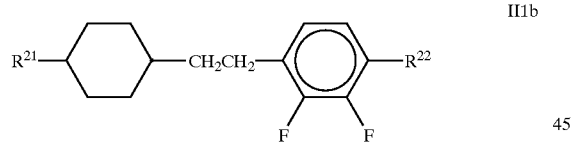

II1b

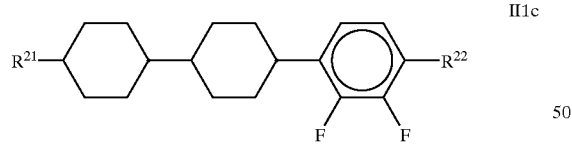

II1c

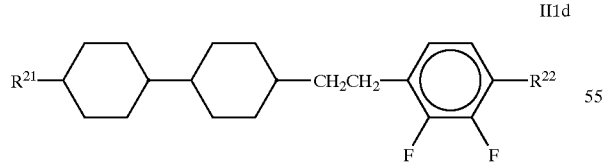

II1d

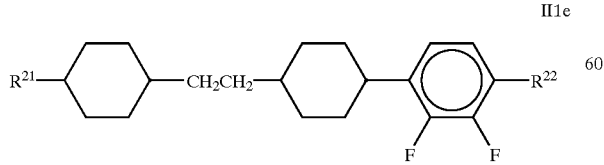

II1e in which $R^{21}$ and $R^{22}$ are as defined above under the formula II and are preferably as defined above under the formula II1.

The liquid-crystal medium particularly preferably comprises one or more compounds selected from the group consisting of the compounds of the formulae III1 to III3:

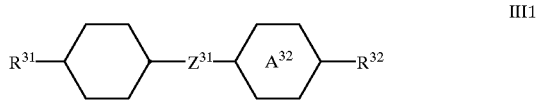

III1

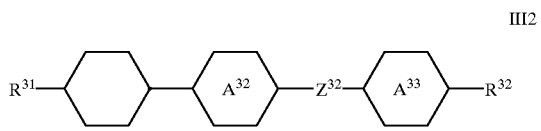

III2

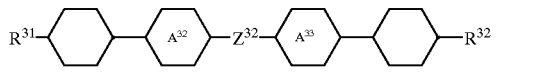

III3 in which $R^{31}$, $R^{32}$, $Z^{31}$, $Z^{32}$,

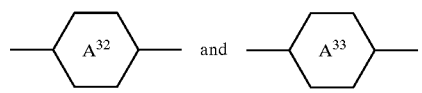

are each as defined above under the formula III.

The liquid-crystal medium especially preferably comprises one or more compounds selected from the group consisting of the compounds of the formulae III1a to III1d, III2a to III2f, III3a to III3d and III4a:

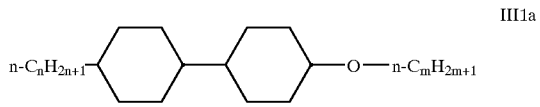

III1a

III1b

III1c

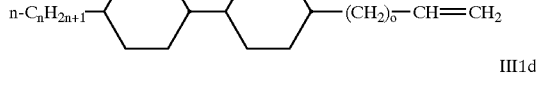

III1d

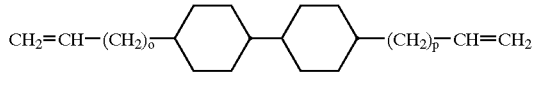

in which n and m are each, independently of one another, from 1 to 5, and o and p are each, independently thereof and independently of one another, from 0 to 3,

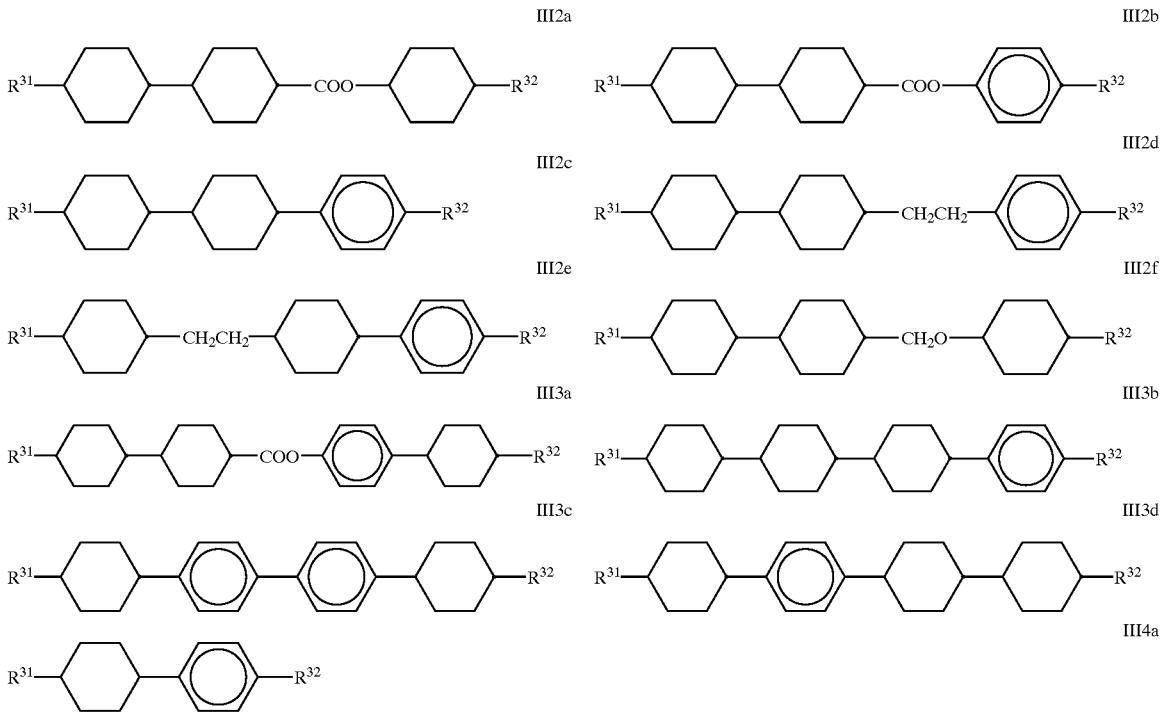

in which $R^{31}$ and $R^{33}$ are each as defined above under the formula III1, and the phenyl rings may optionally be fluorinated, but not in such a way that the compounds are identical with those of the formula II and their sub-formulae. $R^{31}$ is preferably n-alkyl having 1 to 5 carbon atoms, particularly preferably having 1 to 3 carbon atoms, and $R^{32}$ is preferably n-alkyl or n-alkoxy having 1 to 5 carbon atoms or alkenyl having 2 to 5 carbon atoms. Of these, particular preference is given to the compounds of the formulae III1a to III1d.

In a preferred embodiment, the liquid-crystal media according to the invention comprise in total, based on the mixture as a whole, from 2% to 70% of compounds of the formula I,
from 5% to 90% of compounds of the formula II, and
from 0% to 70% of compounds of the formula III.

Here, as in the entire present application, the term compounds, for clarification also written as compound(s), means both one compound and a plurality of compounds, unless expressly stated otherwise.

The individual compounds here are preferably employed in concentrations of from 1% to 30%, preferably from 2% to 20% and particularly preferably from 4% to 16%.

In a preferred embodiment, the liquid-crystal media particularly preferably comprise in total from 5% to 65% of compounds of the formula I,
from 10% to 60% of compounds of the formula II and
from 10% to 60% of compounds of the formula III.

In this embodiment, the liquid-crystal media very particularly preferably comprise in total from 9% to 30% of compounds of the formula I,
from 50% to 60% of compounds of the formula II, and
from 30% to 55% of compounds of the formula III.

In a particularly preferred embodiment, which may be identical and preferably is identical with the preferred embodiments described above for the preferred concentration ranges, the liquid-crystal media comprise one or more compounds of the formula II and
one or more compounds of the formula II1a and/or
    one or more compounds of the formula II1c and
one or more compounds selected from the group consisting of the compounds of the formulae III1a to III1c and/or
    one or more compounds selected from the group consisting of the compounds of the formulae III2 to III3 and/or
one or more compounds selected from the group consisting of the compounds of the formulae I1c to I1e, preferably Ic, and/or
    one or more compounds selected from the group consisting of the compounds of the formulae I4a to I4e, preferably from the group consisting of the formulae I4b and I4e, particularly preferably both of the formulae I4b and also I4e, and
one or more compounds of the formula II, preferably selected from the group consisting of the compounds of the formulae II1a and II1c, and/or
one or more compounds selected from the group consisting of the compounds of the formulae III1a to III1d, III2a to III2f, III3a to III3d and III4a, in particular from the group consisting of the compounds of the formulae III1a to III1d, III2a, III2f, III3a, III3b and III3d, very particularly of the formulae III2f and/or III3d.

Particular preference is given here to liquid-crystal media which comprise one or more compounds of the formula I1, in particular in each case in concentrations of from 6% to 20% per compound,
one or more compounds of the formula I1b, in particular in each case in concentrations of from 4% to 18% per compound,
one or more compounds of the formula II1a, in particular in each case in concentrations of from 3% to 10% per compound, one or more compounds of the formula III1c, in particular in each case in concentrations of from 3% to 12% per compound, preferably in each case at least one compound in which $R^{21}$ is alkyl having 1 to 3 carbon atoms and $R^{22}$ is alkoxy having 1 to 3 carbon atoms and in which $R^{23}$ is alkyl having 1 to 3 carbon atoms and $R^{32}$ is alkyl having 1 to 3 carbon atoms, one or more compounds of the formulae III1a and/or III1c, in particular in concentrations of from 4% to 15% per compound, preferably in each case at least one compound of each of the formulae III1a and III1c, and one or more compounds of the formula III2a.

The liquid-crystal media according to the invention preferably have nematic phases of in each case from −20° C. to 80° C., preferably from −30° C. to 80° C. and very particularly preferably from −40° C. to 90° C. The term "have a nematic phase" here means firstly that no smectic phase and no crystallization are observed at low temperatures at the corresponding temperature and secondly also that no clearing occurs on heating from the nematic phase. The investigation at low temperatures is carried out in a flow viscometer at the corresponding temperature and checked by storage in test cells having a layer thickness corresponding to the electro-optical application for at least 100 hours. At high temperatures, the clearing point is measured in capillaries by conventional methods.

Furthermore, the liquid-crystal media according to the invention are characterized by low optical anisotropy values. The birefringence values are typically less than or equal to 0.100, preferably less than or equal to 0.080 and very particularly preferably less than or equal to 0.075.

In addition, the liquid-crystal media according to the invention typically have relatively low values for the Freedericksz threshold voltage of less than or equal to 3.0 V, preferably less than or equal to 2.7 V, particularly preferably less than or equal to 2.6 V and very particularly preferably less than or equal to 2.5 V.

These preferred values for the individual physical properties are also observed in each case combined with one another. Thus, media according to the invention typically have, in particular, the following property combinations:

|  | Phase | Δn | Freedericksz threshold/V |
|---|---|---|---|
| According to the invention | ≦−20 to ≧80 | ≦0.10 | ≦2.5 |
| Preferably | ≦−30 to ≧90 | ≦0.08 | ≦3.2 |
| Particularly preferably | ≦−40 to ≧80 | ≦0.07 | ≦2.8 | where here, as throughout the application, "≦" means less than or equal to and "≧" means greater than or equal to.

The above-mentioned preferred concentration ranges particularly preferably also apply to this preferred combination of compounds.

Through a suitable choice of the meanings of the parameters of the compounds, in particular of $R^{11}$, $R^{12}$, $R^{21}$, $R^{21}$, $R^{31}$. $R^{32}$, $L^1$ and $L^2$, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio of the elastic constants $k_{33}$ (bend) and $k_{11}$ (splay) compared with alkyl or alkoxy radicals. 4-alkenyl radicals, 3-alkenyl radicals and the like generally give lower threshold voltages and smaller values of $k_{33}/k_{11}$ compared with alkyl and alkoxy radicals.

A —CH$_2$CH$_2$— group generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa.

In the present application, the term dielectrically positive compounds means compounds having a Δε of >1.5, dielectrically neutral compounds means those in which −1.5≦Δε≦1.5, and dielectrically negative compounds means those having a Δε<−1.5. The dielectric anisotropy of the compounds is determined here by dissolving 10% of the compounds in a liquid-crystalline host and determining the capacitance of this mixture at 1 kHz in at least one test cell having a thickness of 10 μm with a homeotropic surface alignment and in at least one test cell having a thickness of 10 μm with a homogeneous surface alignment. The measurement voltage is typically from 0.5 V to 1.0 V, but is always less than the capacitive threshold of the respective liquid-crystal mixture.

The host mixture used for dielectrically positive compounds is ZLI-4792 and the host mixture used for dielectrically neutral and dielectrically negative compounds is ZLI-3086, both from Merck KGaA, Germany. The change in the dielectric constants of the host mixture after addition of the compound to be investigated and extrapolation to 100% of the compound employed gives the values for the respective compounds to be investigated.

The term threshold voltage usually relates to the optical threshold for 10% relative contrast ($V_{10}$).

In relation to the liquid-crystal mixtures of negative dielectric anisotropy, however, the term threshold voltage in the present application is used for the capacitive threshold voltage ($V_0$), also known as the Freedericksz threshold, unless explicitly stated otherwise.

The liquid-crystal media according to the invention may, if necessary, also comprise further additives and optionally also chiral dopants in the conventional amounts. The amount of these additives employed is in total from 0% to 10%, based on the amount of the mixture as a whole, preferably from 0.1% to 6%. The concentrations of the individual compounds employed are preferably from 0.1 to 3%. The concentration of this and similar additives is not taken into account when indicating the concentrations and the concentration ranges of the liquid-crystal compounds in the liquid-crystal media.

The compositions consist of a plurality of compounds, preferably from 3 to 30, particularly preferably from 6 to 20 and very particularly preferably from 10 to 16 compounds, which are mixed in a conventional manner. In general, the desired amount of the components used in lesser amount is dissolved in the components making up the principal constituent, advantageously at elevated temperature. If the selected temperature is above the clearing point of the principal constituents, the completion of the dissolution process is particularly easy to observe. However, it is also possible to prepare the liquid-crystal mixtures in other conventional ways, for example using premixes or from a so-called "multibottle system".

By means of suitable additives, the liquid-crystal phases according to the invention can be modified in such a way that they can be employed in any type of ECB display and in particular of PA LCDs and IPS display that has been disclosed hitherto.

The examples below serve to illustrate the invention without representing a restriction. In the examples, the melting point T (C,N), the transition from the smectic (S) phase to the nematic (N) phase T(S,N) and the clearing point T (N,I) of a liquid-crystal substance is indicated in degrees Celsius, and physical properties are the values at 20° C., unless explicitly stated otherwise.

All temperature differences are correspondingly differential degrees ° C., unless explicitly stated otherwise. Moreover, in the foregoing and in the following examples, all temperatures are set forth uncorrected in degrees Celsius; and, unless otherwise indicated, all parts and percentages are by weight.

All concentrations in this application, unless explicitly stated otherwise, are given in per cent by weight and relate to the corresponding mixture as a whole. All physical properties are and have been determined in accordance with "Merck Liquid Crystals, Physical Properties of Liquid Crystals", status November 1997, Merck KGaA, Germany, and apply to a temperature of 20° C., unless explicitly stated otherwise. $\Delta n$ is determined at 589 nm and $\Delta \epsilon$ at 1 kHz. The threshold voltages and the other electro-optical properties were determined in test cells produced at Merck KGaA, Germany, using white light by means of a commercial measuring instrument from Otsuka, Japan. To this end, cells were selected having, depending on the $\Delta n$ of the liquid crystals, a thickness corresponding to an optical retardation $d.\Delta n$ of the cells of about 0.50 $\mu$m. The cells were operated in so-called normally white mode with parallel polarisers. The characteristic voltages were all determined with perpendicular viewing. The threshold voltage has been indicated as $V_{10}$ for 10% relative contrast, the mid-grey voltage $V_{50}$ for 50% relative contrast and the saturation voltage $V_{90}$ for 90% relative contrast.

In the case of the liquid-crystal media of negative dielectric anisotropy, the threshold voltage was determined as the capacitive threshold $V_0$ (also known as the Freedericksz threshold) in cells with a liquid-crystal layer aligned homeotropically by means of lecithin.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is indicated. In individual cases, the acronym for the parent structure is followed, separated by a hyphen, by a code for the substituents $R^1$, $R^2$, $L^1$ and $L^2$:

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure of all applications, patents and publications, cited above, and of corresponding German Application No. 100 47 059.9, filed Sep. 22, 2000 are hereby incorporated by reference.

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nmF | $C_nH_{2n+1}$ | $C_mH_{2m+1}$ | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| nEsN | $C_rH_{2r+1}$—O—$C_sH_{2s}$— | CN | H | H |
| nAm | $C_nH_{2n+1}$ | $COOC_mH_{2m+1}$ | H | H |
| nF.Cl | $C_nH_{2n+1}$ | Cl | H | F |

TABLE A

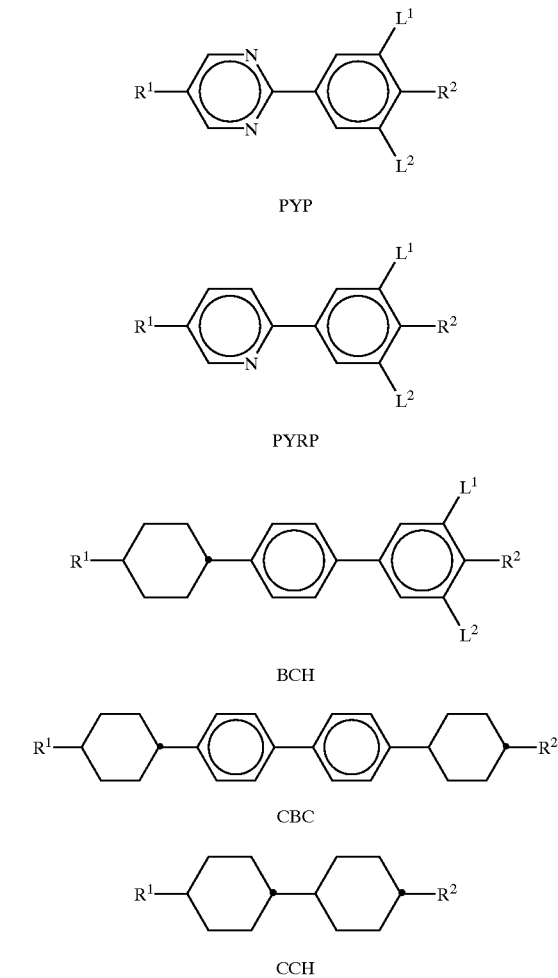

PYP

PYRP

BCH

CBC

CCH

TABLE A-continued
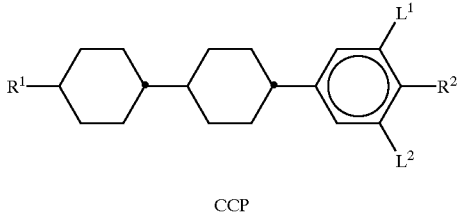
CCP
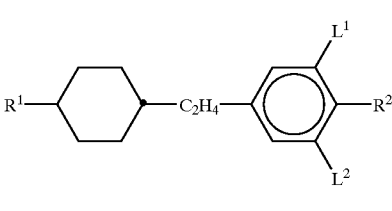
CP
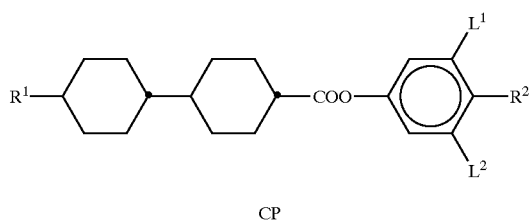
CPTP
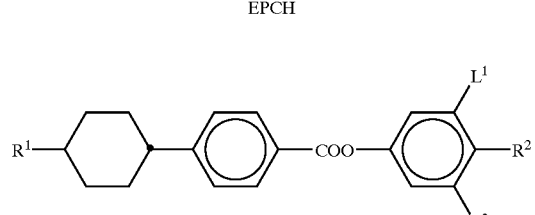
CEPTP
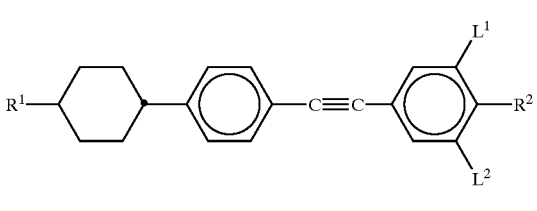
D
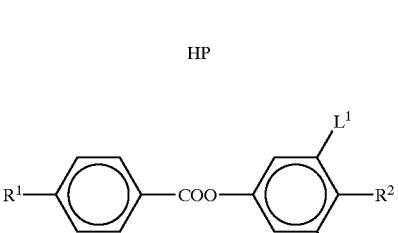
ECCP
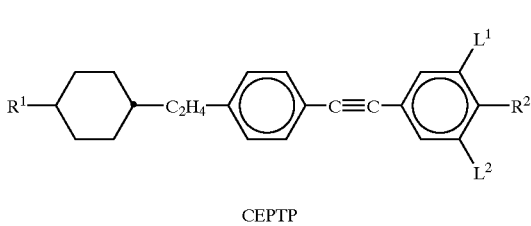
CECP
TABLE A-continued
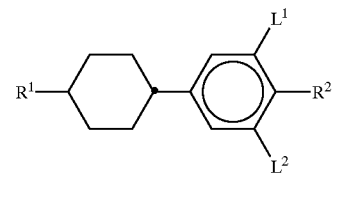
EPCH
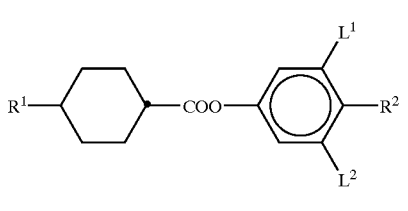
HP
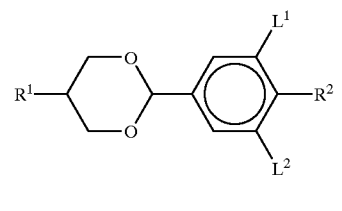
ME
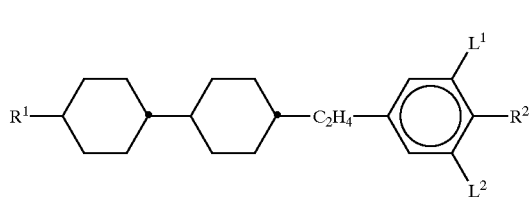
PCH
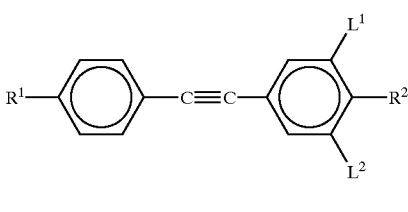
PDX
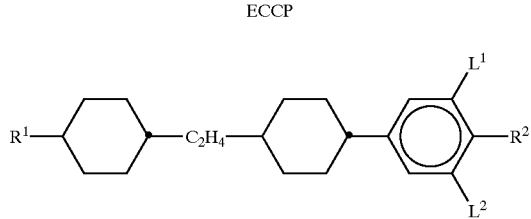
PTP TABLE A-continued
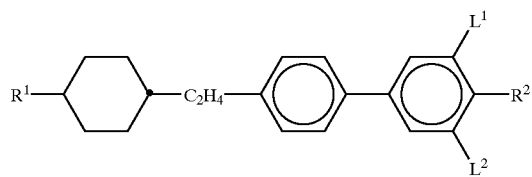
BECH
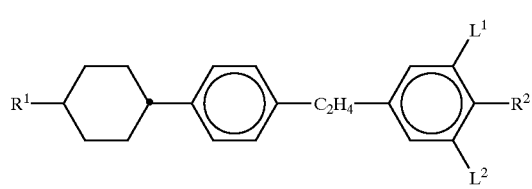
EBCH
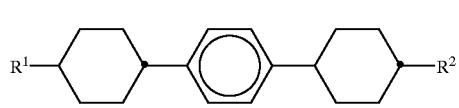
TABLE A-continued
CPC
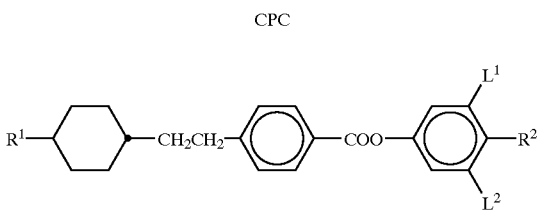
EHP
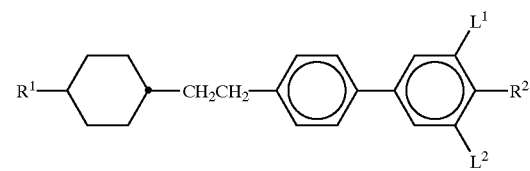
BEP
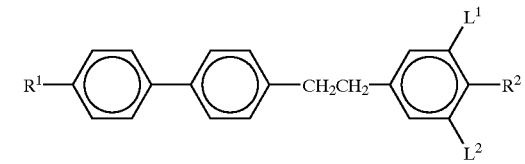
ET
TABLE B
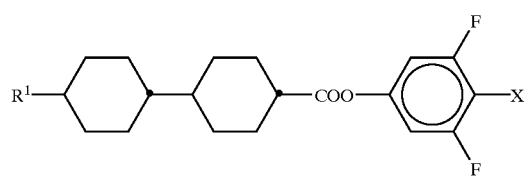
CCZU-n-X
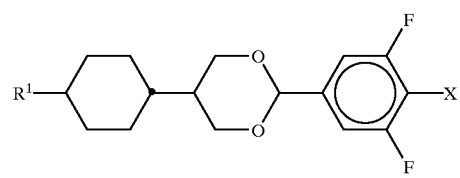
CDU-n-X
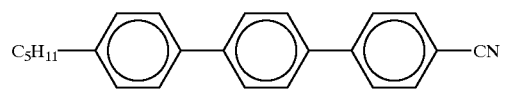
T15
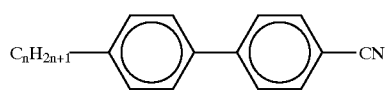
K3n TABLE B-continued
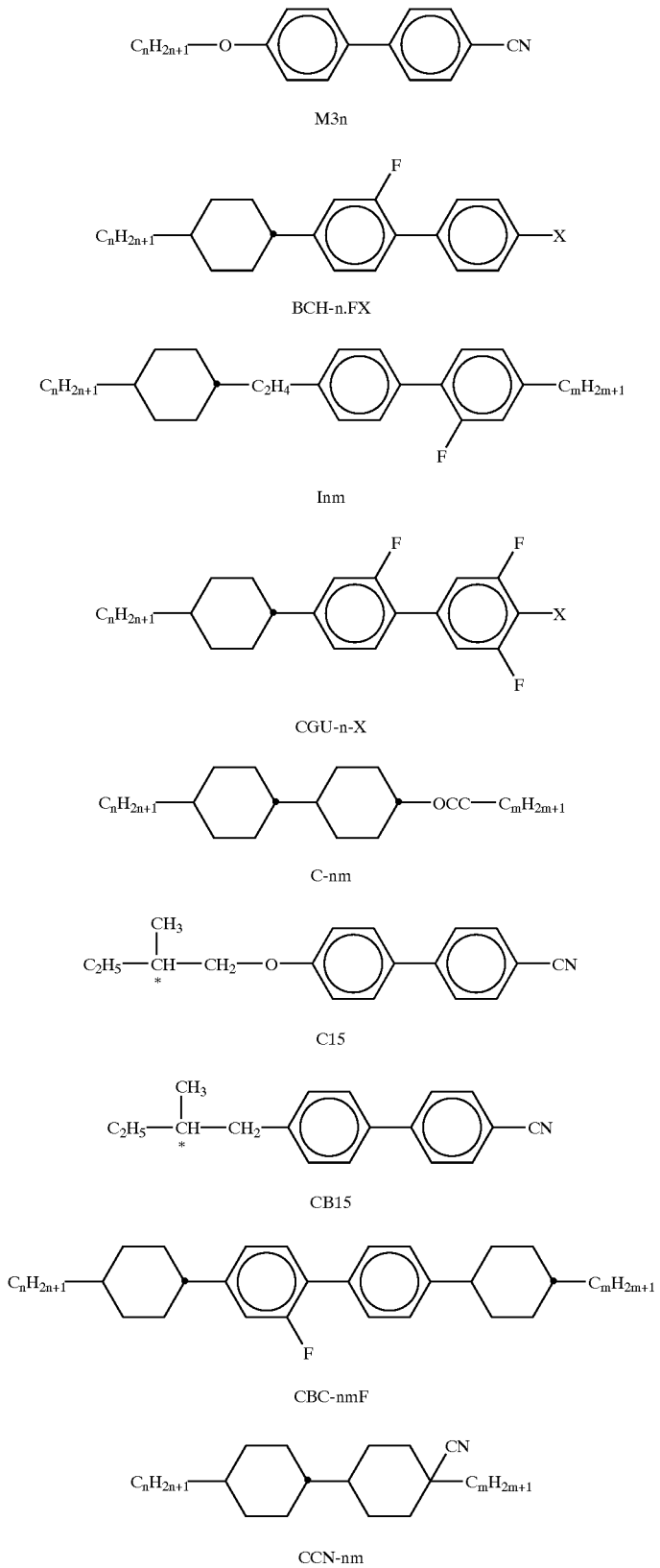

TABLE B-continued
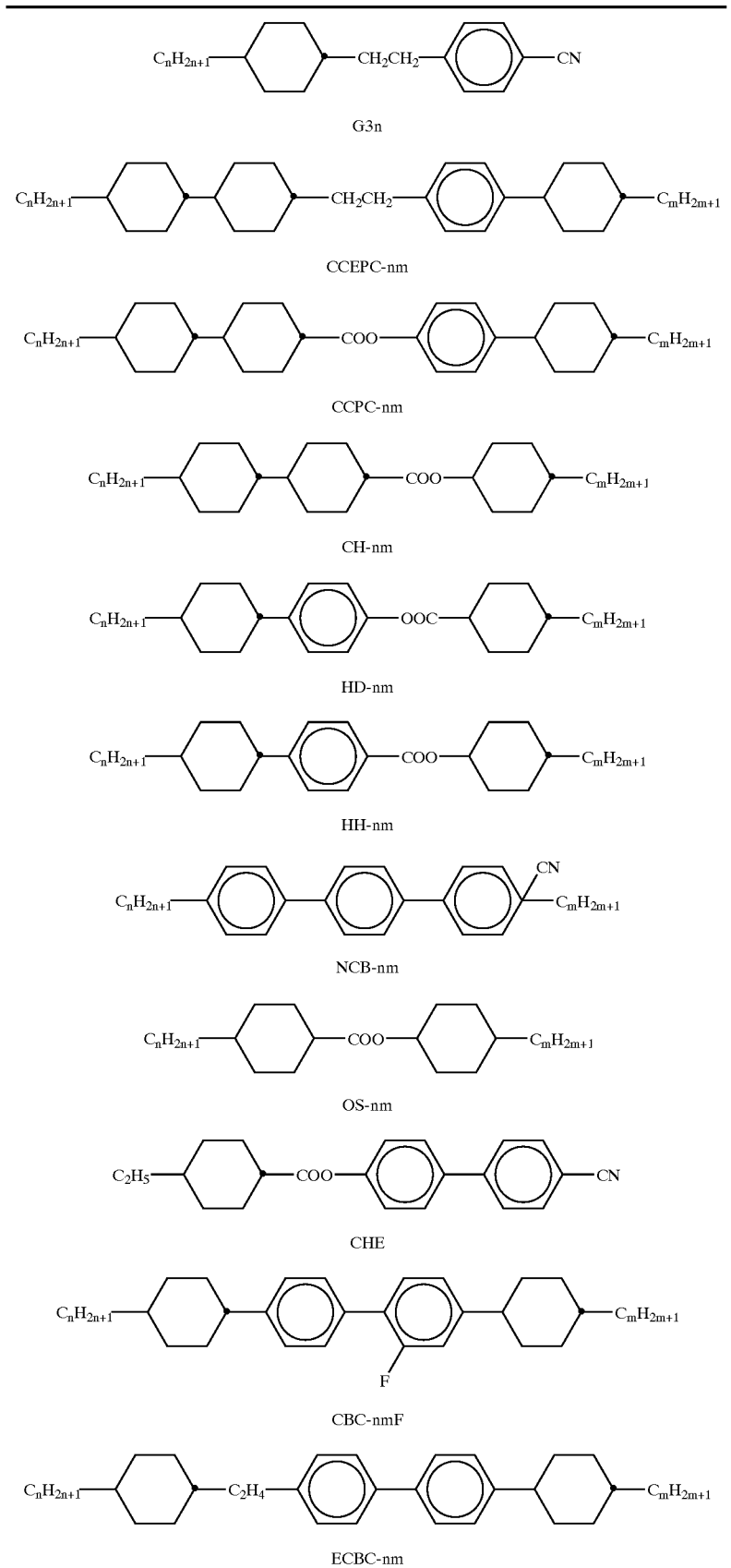

TABLE B-continued
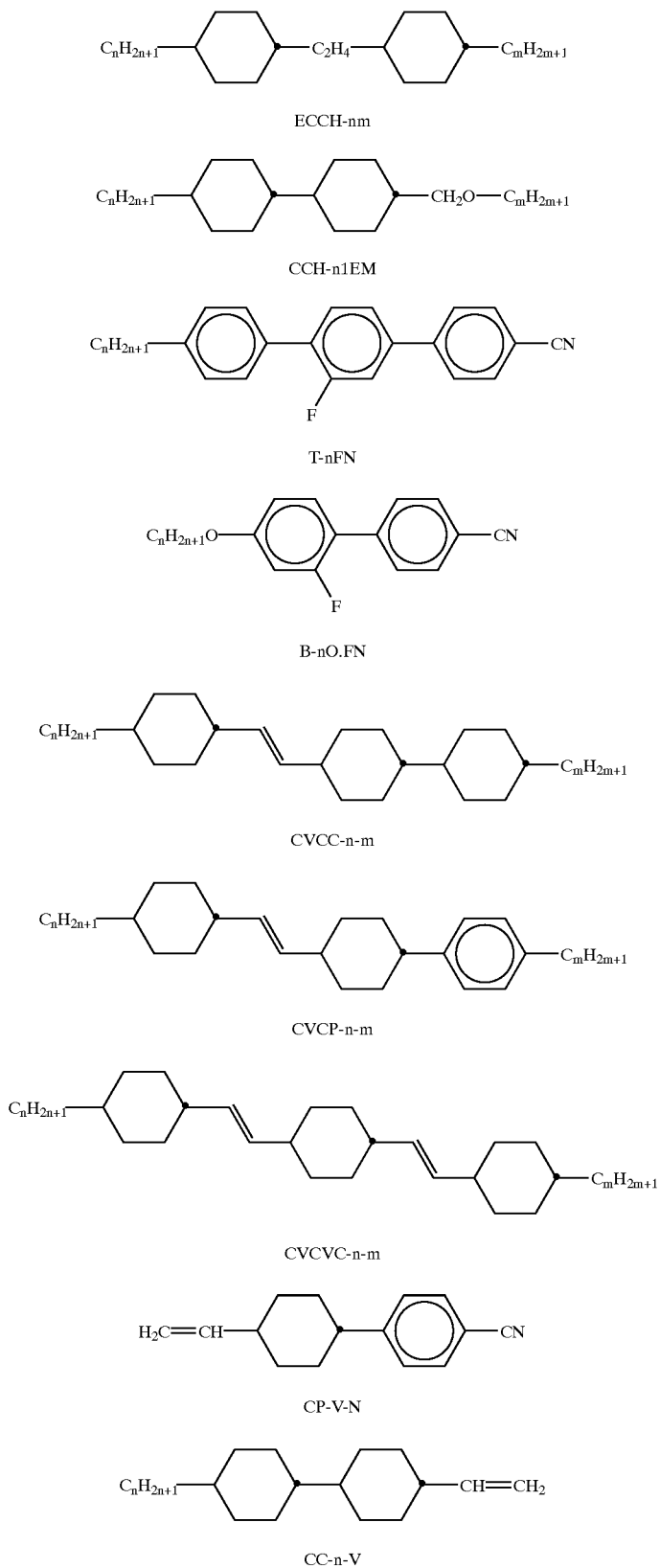

TABLE B-continued
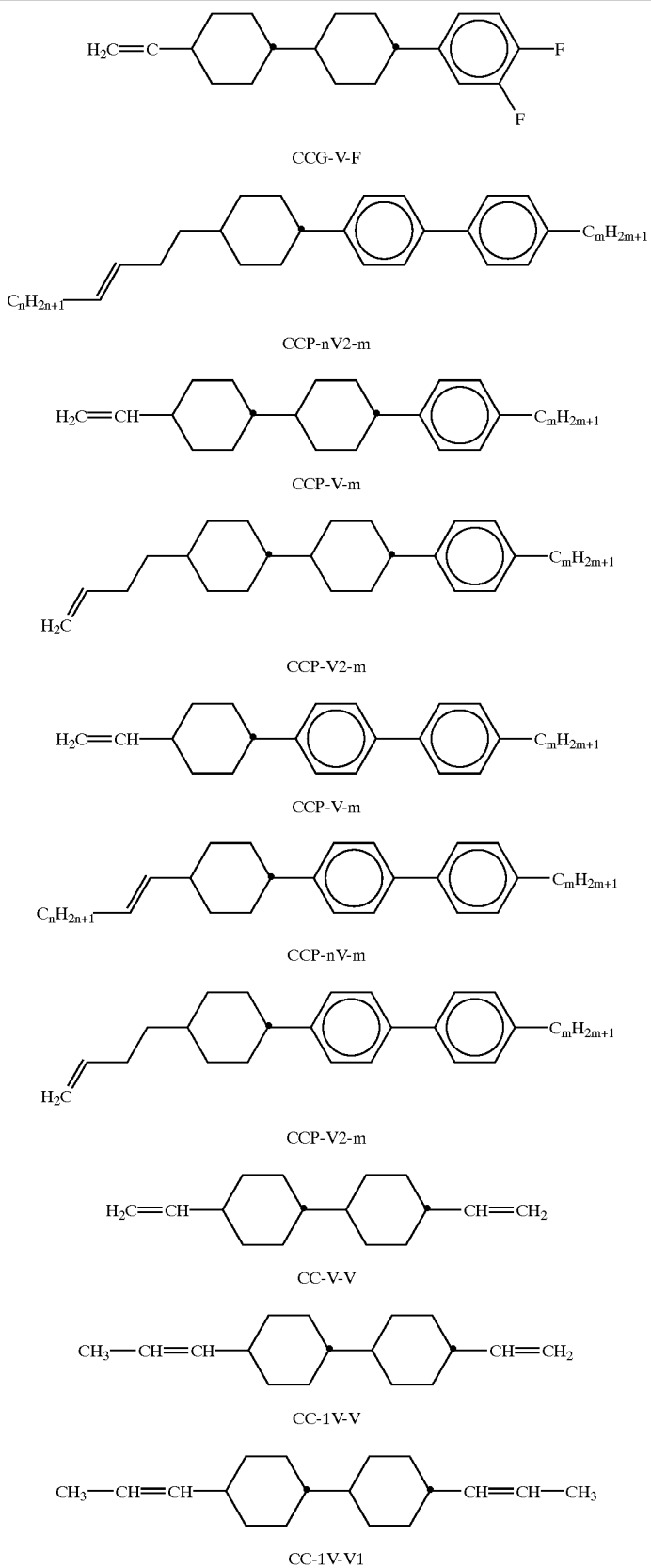

TABLE B-continued

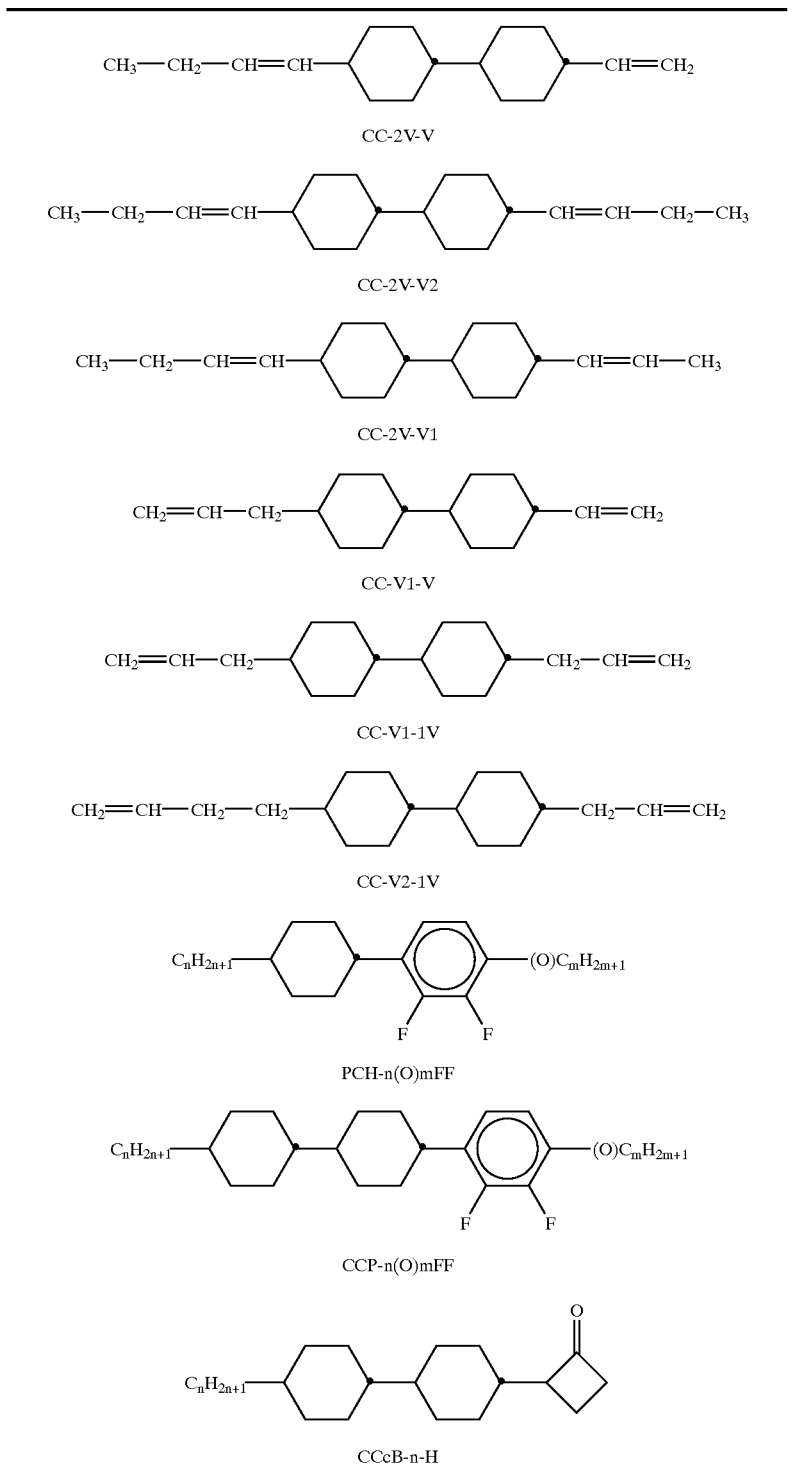

EXAMPLES

Δn denotes optical anisotropy (589 nm, 20° C.), Δε denotes the dielectric anisotropy (1 kHz, 20° C.), H. R. denotes the voltage holding ratio (at 100° C., after 5 minutes in the oven, 1 V), $V_{10}$, $V_{50}$ and $V_{90}$ denote the threshold voltage, mid-grey voltage and saturation voltage respectively, and the capacitive threshold voltage $V_0$ were determined at 20° C.

SUBSTANCE EXAMPLES

Example 1

Preparation of 2-trans-4-(trans-4-n-pentylcyclohexyl) cyclohexyl-4-(2-trans-4-n-propylcyclohexylethyl) cyclobutanone Firstly, trans-4-(trans-4-n-pentylcyclohexyl)cyclohexylcyclobutanone was prepared as described in DE 199 55 932.

53.523 g of 3-bromotriphenylphosphonium bromide (Aldrich, No. 13,525-9) in 650 ml of ethylene glycol dimethyl ether (for synthesis, Merck-Schuchardt, Art. No. 8000 856) were introduced under nitrogen into a 1 l round-bottomed flask with stirrer at an ambient temperature of about 22° C. 9.039 g of a 60% suspension of sodium hydride in paraffin oil (Merck-Schuchardt, Art. No. 814 552) were then added. 29.883 g of trans-4-(trans-4-n-pentylcyclohexyl)cyclohexylmethyl aldehyde prepared in house were subsequently added in portions at ambient temperature. After a short time, the temperature in the reaction vessel increased. After 5 minutes, it reached a maximum value of 49° C. The mixture was then stirred at this temperature for a further 15 minutes. After the temperature then began to drop, the mixture was warmed to 70° C. and stirred at this temperature for 4 hours. The completeness was checked by thin-layer chromatography (TLC) (heptane/$KMnO_4$). The reaction mixture was then allowed to cool to ambient temperature and subsequent poured onto ice with hydrochloric acid. The aqueous phase was taken off and extracted with MTB ether. The combined organic phases were washed once with saturated aqueous sodium chloride solution, dried over sodium sulfate, filtered and evaporated in a rotary evaporator. The crude product obtained was 70.9 g of a white slurry. This was purified by column chromatography with hexane over silica gel. The corresponding fractions were combined, and the solvent was removed in a rotary evaporator. The yield was 30.8 g (94.5% of theory) of the cyclopropylene compound, a colorless, clear liquid.

The resultant 30.8 g of cyclopropylene compound were dissolved in 900 ml of dichloromethane for analysis (Merck-Schuchardt, Art. No. 106 050) at an ambient temperature of about 22° C. and then cooled to 5° C. in a 2 l round-bottomed flask in a cold bath. At this temperature, 47.0 g of 3-chloroperbenzoic acid (Aldrich, No. 27,303-1) were added with stirring. The reaction was exothermic. The reaction solution was subsequently stirred at this temperature for 3 hours. The completeness of the reaction was checked by TLC (eluent: hexane). Distilled water was then added, and the aqueous phase was separated and extracted with dichloromethane. The combined organic extracts were extracted with 15% aqueous sodium hydrogensulfide solution. The organic phase became milky in the process. It was then washed with distilled water and 3 times with 5% aqueous ammonium iron(II) sulfate solution. This removed all peroxides present, as checked by means of a peroxide test. The organic phase was dried using sodium sulfate, filtered and evaporated to 59.4 g in a rotary evaporator. The product was subsequently isolated by column chromatography in toluene on silica gel, and the corresponding fractions were evaporated in a rotary evaporator. 13.3 g of crude crystals were obtained. Recrystallization from ethanol at −20° C. gave 11.3 g of trans-4-(trans-4-n-pentylcyclohexyl)-cyclohexylcyclobutanone having a phase sequence C 80° C. $S_B$ 132° C. 1 as white crystals. The compound has an extrapolated clearing point of 48° C.

Examples 2 to 39

The following are prepared analogously to Example 1:

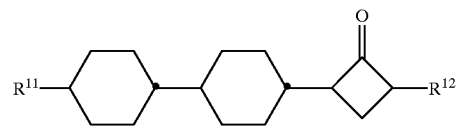

| No. | $R^{11}$ | $R^{12}$ | Phase sequence T/° C. | T(N, I)/° C. * |
|---|---|---|---|---|
| 2 | $CH_3$ | H | | |
| 3 | $C_2H_5$ | H | C 82 $S_B$ 137 I | 6 |
| 1 | n-$C_3H_7$ | H | C 63 $S_B$ 137 I | 31 |
| 4 | n-$C_4H_9$ | H | C 80 $S_{mB}$ 132 | 48 |
| 5 | n-$C_5H_{11}$ | H | | |
| 6 | $CH_3O$ | H | | |
| 7 | $C_2H_5O$ | H | | |
| 8 | n-$C_3H_7O$ | H | | |
| 9 | n-$C_4H_9O$ | H | | |
| 10 | $CH_2$=CH | H | | |
| 11 | E-$CH_3$—$CH_2$=CH | H | | |
| 12 | $CH_2$=CH—O | H | | |
| 13 | $CH_2$=CH—$CH_2$O | H | | |
| 14 | $CH_3$ | $CH_3$ | | |
| 15 | $C_2H_5$ | $CH_3$ | | |
| 16 | n-$C_3H_7$ | $CH_3$ | | |
| 17 | n-$C_4H_9$ | $CH_3$ | | |
| 18 | n-$C_5H_{11}$ | $CH_3$ | | |
| 19 | $CH_3O$ | $CH_3$ | | |
| 20 | $C_2H_5O$ | $CH_3$ | | |
| 21 | n-$C_3H_7O$ | $CH_3$ | | |
| 22 | n-$C_4H_9O$ | $CH_3$ | | |
| 23 | $CH_2$=CH | $CH_3$ | | |
| 24 | E-$CH_3$—CH=CH | $CH_3$ | | |
| 25 | $CH_2$=CH—O | $CH_3$ | | |
| 26 | $CH_2$=CH—$CH_2$O | $CH_3$ | | |
| 27 | $CH_3$ | $OCH_3$ | | |
| 28 | $C_2H_5$ | $C_3H_7$ | | |
| 29 | n-$C_3H_7$ | $C_3H_7$ | | |

-continued

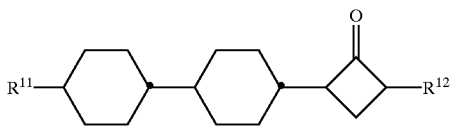

| No. | R¹¹ | R¹² | Phase sequence T/° C. | T(N, I)/° C. * |
|---|---|---|---|---|
| 30 | n-C₄H₉ | C₃H₇ | | |
| 31 | n-C₅H₁₁ | C₃H₇ | | |
| 32 | CH₃O | C₃H₇ | | |
| 33 | C₂H₅O | C₃H₇ | | |
| 34 | n-C₃H₇O | C₃H₇ | | |
| 35 | n-C₄H₉O | C₃H₇ | | |
| 36 | CH₂=CH | C₃H₇ | | |
| 37 | E-CH₃—CH=OH | C₃H₇ | | |
| 38 | CH₂=CH—O | C₃H₇ | | |
| 39 | CH₂=CH—CH₂O | C₃H₇ | | |

Note:
* clearing point/° C. extrapolated from 10% solution in ZLI-4792.

Examples 40 to 78

The following are prepared analogously to Example 1:

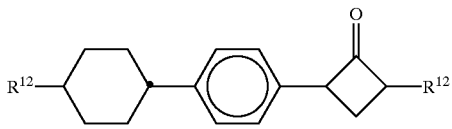

| No. | R¹¹ | R¹² | Phase sequence T/° C. | T(N, I)/° C. * |
|---|---|---|---|---|
| 40 | CH₃ | H | | |
| 41 | C₂H₅ | H | | |
| 42 | n-C₃H₇ | H | C 44 I | −44 |
| 43 | n-C₄H₉ | H | | |
| 44 | n-C₅H₁₁ | H | | |
| 45 | CH₃O | H | | |
| 46 | C₂H₅O | H | | |
| 47 | n-C₃H₇O | H | | |
| 48 | n-C₄H₉O | H | | |
| 49 | CH₂=CH | H | | |
| 50 | E-CH₃—CH₂=CH | H | | |
| 51 | CH₂=CH—O | H | | |
| 52 | CH₂=CH—CH₂O | H | | |
| 53 | CH₃ | CH₃ | | |
| 54 | C₂H₅ | CH₃ | | |
| 55 | n-C₃H₇ | CH₃ | | |
| 56 | n-C₄H₉ | CH₃ | | |
| 57 | n-C₅H₁₁ | CH₃ | | |
| 58 | CH₃O | CH₃ | | |
| 59 | C₂H₅O | CH₃ | | |
| 60 | n-C₃H₇O | CH₃ | | |
| 61 | n-C₄H₉O | CH₃ | | |
| 62 | CH₂=CH | CH₃ | | |
| 63 | E-CH₃—CH=CH | CH₃ | | |
| 64 | CH₂=CH—O | CH₃ | | |
| 65 | CH₂=CH—CH₂O | CH₃ | | |
| 66 | CH₃ | OCH₃ | | |
| 67 | C₂H₅ | C₃H₇ | | |
| 68 | n-C₃H₇ | C₃H₇ | | |
| 69 | n-C₄H₉ | C₃H₇ | | |
| 70 | n-C₅H₁₁ | C₃H₇ | | |
| 71 | CH₃O | C₃H₇ | | |
| 72 | C₂H₅O | C₃H₇ | | |

-continued

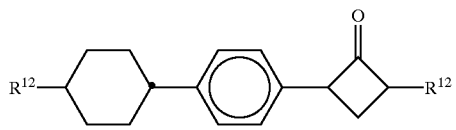

| No. | R¹¹ | R¹² | Phase sequence T/° C. | T(N, I)/° C. * |
|---|---|---|---|---|
| 73 | n-C₃H₇O | C₃H₇ | | |
| 74 | n-C₄H₉O | C₃H₇ | | |
| 75 | CH₂=CH | C₃H₇ | | |
| 76 | E-CH₃—CH=CH | C₃H₇ | | |
| 77 | CH₂=CH—O | C₃H₇ | | |
| 78 | CH₂=OH—CH₂O | C₃H₇ | | |

Note:
* clearing point/° C. extrapolated from 10% solution in ZLI-4792.

Examples 79 to 117

The following are prepared analogously to Example 1:

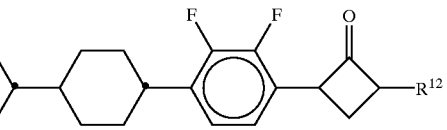

| No. | R¹¹ | R¹² | Phase sequence T/° C. | T(N, I)/° C. * |
|---|---|---|---|---|
| 79 | CH₃ | H | | |
| 80 | C₂H₅ | H | | |
| 81 | n-C₃H₇ | H | C 108 S$_B$ 124 I | 107 |
| 82 | n-C₄H₉ | H | | |
| 83 | n-C₅H₁₁ | H | | |
| 84 | CH₃O | H | | |
| 85 | C₂H₅O | H | | |
| 86 | n-C₃H₇O | H | | |
| 87 | n-C₄H₉O | H | | |
| 88 | CH₂=CH | H | | |
| 89 | E-CH₃—CH₂=CH | H | | |
| 90 | CH₂=CH—O | H | | |
| 91 | CH₂=CH—CH₂O | H | | |
| 92 | CH₃ | CH₃ | | |
| 93 | C₂H₅ | CH₃ | | |
| 94 | n-C₃H₇ | CH₃ | | |
| 95 | n-C₄H₉ | CH₃ | | |
| 96 | n-C₅H₁₁ | CH₃ | | |
| 97 | CH₃O | CH₃ | | |
| 98 | C₂H₅O | CH₃ | | |
| 99 | n-C₃H₇O | CH₃ | | |
| 100 | n-C₄H₉O | CH₃ | | |
| 101 | CH₂=CH | CH₃ | | |
| 102 | E-CH₃—CH=CH | CH₃ | | |
| 103 | CH₂=CH—O | CH₃ | | |
| 104 | CH₂=CH—CH₂O | CH₃ | | |
| 105 | CH₃ | OCH₃ | | |
| 106 | C₂H₅ | C₃H₇ | | |
| 107 | n-C₃H₇ | C₃H₇ | | |
| 108 | n-C₄H₉ | C₃H₇ | | |
| 109 | n-C₅H₁₁ | C₃H₇ | | |
| 110 | CH₃O | C₃H₇ | | |
| 111 | C₂H₅O | C₃H₇ | | |
| 112 | n-C₃H₇O | C₃H₇ | | |
| 113 | n-C₄H₉O | C₃H₇ | | |
| 114 | CH₂=CH | C₃H₇ | | |
| 115 | E-CH₃—CH=CH | C₃H₇ | | |
| 116 | CH₂=CH—O | C₃H₇ | | |
| 117 | CH₂=CH—CH₂O | C₃H₇ | | |

Note:
* clearing point/° C. extrapolated from 10% solution in ZLI-4792.

MIXTURE EXAMPLES

Example M 1

| Compound/abbreviation | Concentration/% by weight | Physical properties |
|---|---|---|
| CCP-302FF | 12.0 | Clearing point (N;I) = 83.0° C. |
| CCP-502FF | 12.0 | $n_e$ (20° C., 589 nm) = 1.5521 |
| CCP-21FF | 6.0 | $\Delta n$ (20° C., 589 nm) = 0.0719 |
| CCP-31FF | 6.0 | $\epsilon_{11}$ (20° C., 1 kHz) = 3.1 |
| CCH-301 | 5.0 | $\Delta \epsilon$ (20° C., 1 kHz) = −2.3 |
| PCH-53 | 20.0 | $k_1$ (20° C.) = 16.8 pN |
| CCH-34 | 5.0 | $k_3/k_1$ (20° C.) = 0.82 |
| CCH-35 | 5.0 | |
| CCcB-3-H | 15.0 | $V_0$ (20° C.) = 2.57 V |
| CH-33 | 2.0 | |
| CH-35 | 3.0 | |
| CH-43 | 3.0 | |
| CH-45 | 2.0 | |
| PCH-504FF | 4.0 | |
| Σ | 100.0 | |

The liquid-crystal medium has excellent applicational properties and is distinguished, in particular, by a very small $\epsilon_{\parallel}$.

Example M 2

| Compound/abbreviation | Concentration/% by weight | Physical properties |
|---|---|---|
| CCP-302FF | 12.0 | Clearing point (N;I) = 81.0° C. |
| CCP-502FF | 12.0 | (S,N) transition < −20° C. |
| CCP-21FF | 5.0 | $n_e$ (20° C., 589 nm) = 1.5540 |
| CCP-31FF | 5.0 | $\Delta n$ (20° C., 589 nm) = 0.0723 |
| CCH-301 | 5.0 | $\epsilon_{11}$ (20° C., 1 kHz) = 3.0 |
| PCH-53 | 20.0 | $\Delta \epsilon$ (20° C., 1 kHz) = −2.2 |
| CCH-34 | 5.0 | |
| CCH-35 | 5.0 | $V_0$ (20° C.) = 2.61 V |
| CCcB-3-H | 10.0 | |
| CH-33 | 2.0 | |
| CH-35 | 3.0 | |
| CH-43 | 3.0 | |
| CH-45 | 2.0 | |
| PCH-504FF | 6.0 | |
| CC-5-V | 5.0 | |
| Σ | 100.0 | |

The liquid-crystal medium has excellent applicational properties and is distinguished, in particular, by a very small $\epsilon_{\parallel}$.

Example M 3

| Compound/abbreviation | Concentration/% by weight | Physical properties |
|---|---|---|
| CCP-302FF | 12.0 | Clearing point (N;I) = 82.6° C. |
| CCP-502FF | 12.0 | (S,N) transition < −30° C. |
| CCP-21FF | 6.0 | $n_e$ (20° C., 589 nm) = 1.5528 |
| CCP-31FF | 6.0 | $\Delta n$ (20° C., 589 nm) = 0.0717 |
| CCH-301 | 5.0 | $\epsilon_{11}$ (20° C., 1 kHz) = 2.9 |
| PCH-53 | 20.0 | $\Delta \epsilon$ (20° C., 1 kHz) = −2.4 |
| CCH-34 | 5.0 | |
| CCH-35 | 5.0 | $V_0$ (20° C.) = 2.58 V |
| CCcB-2-H | 4.0 | |
| CCcB-3-H | 6.0 | |
| CCcB-5-H | 5.0 | |
| CH-33 | 2.0 | |
| CH-35 | 3.0 | |
| CH-43 | 3.0 | |
| CH-45 | 2.0 | |
| PCH-504FF | 4.0 | |
| Σ | 100.0 | |

The liquid-crystal medium has excellent applicational properties and is distinguished, in particular, by a very small $\epsilon_{\parallel}$.

Comparative Example CM 1

| Compound/abbreviation | Concentration/% by weight | Physical properties |
|---|---|---|
| CCP-302FF | 14.0 | Clearing point (N;I) = 85.5° C. |
| CCP-502FF | 14.0 | (S,N) transition < −40° C. |
| CCP-21FF | 5.0 | $n_e$ (20° C., 589 nm) = 1.5535 |
| CCP-31FF | 11.0 | $\Delta n$ (20° C, 589 nm) = 0.0769 |
| PCH-502FF | 14.0 | $\epsilon_{11}$ (20° C., 1 kHz) = 3.3 |
| CCH-301 | 11.0 | $\Delta \epsilon$ (20° C., 1 kHz) = −3.0 |
| CCH-501 | 8.0 | $k_1$ (20° C.) = 15.4 pN |
| CC-5-V | 4.0 | $k_3/k_1$ (20° C.) = 1.08 |
| PCH-53 | 9.0 | |
| CH-35 | 2.0 | $V_0$ (20° C.) = 2.48 V |
| CH-43 | 3.0 | |
| CCH-35 | 5.0 | |
| Σ | 100.0 | |

Comparative Example CM 2

| Compound/abbreviation | Concentration/% by weight | Physical properties |
|---|---|---|
| CCP-302FF | 10.0 | Clearing point (N;I) = 82.0° C. |
| CCP-502FF | 10.0 | (S,N) transition < 20° C. |
| CCP-21FF | 14.0 | $n_e$ (20° C., 589 nm) = 1.5581 |
| CCP-31FF | 13.0 | $\Delta n$ (20° C., 589 nm) = 0.0789 |
| PCH-302FF | 12.0 | $\epsilon_{11}$ (20° C., 1 kHz) = 3.3 |
| CCH-35 | 19.0 | $\Delta \epsilon$ (20° C., 1 kHz) = −2.7 |
| CCH-301 | 10.0 | $k_1$ (20° C.) = 16.9 pN |
| PCH-301 | 12.0 | $k_3/k_1$ (20° C.) = 0.86 |
| Σ | 100.0 | |
| | | $V_0$ (20° C.) = 2.63 V |

Comparative Example CM 3

| Compound/abbreviation | Concentration/% by weight | Physical properties |
|---|---|---|
| CCP-302FF | 15.0 | Clearing point (N;I) = 85.0° C. |
| CCP-502FF | 15.0 | (S,N) transition < 20° C. |
| CCP-31FF | 12.0 | $n_e$ (20° C., 589 nm) = 1.5461 |
| PCH-302FF | 4.0 | $\Delta n$ (20° C., 589 nm) = 0.0730 |
| PCH-502FF | 12.0 | $\epsilon_{11}$ (20° C., 1 kHz) = 3.3 |

-continued

| Compound/abbreviation | Concentration/% by weight | Physical properties | |
|---|---|---|---|
| CCH-301 | 10.0 | Δε (20° C., 1 kHz) = | −3.1 |
| CCH-501 | 15.0 | $k_1$ (20° C.) = | 15.7 pN |
| CCH-34 | 17.0 | $k_3/k_1$ (20° C.) = | 1.03 |
| Σ | 100.0 | | |
| | | $V_0$ (20° C.) = | 2.41 V |

Comparative Example CM 4

| Compound/abbreviation | Concentration/% by weight | Physical properties | |
|---|---|---|---|
| CCP-302FF | 14.0 | Clearing point (N;I) = | 83.5° C. |
| CCP-502FF | 14.0 | (S,N) transition < | 20° C. |
| CCP-21FF | 13.0 | $n_e$ (20° C., 589 nm) = | 1.5536 |
| CCP-31FF | 6.0 | Δn (20° C., 589 nm) = | 0.0776 |
| PCH-502FF | 15.0 | $ε_{11}$ (20° C., 1 kHz) = | 3.3 |
| CCH-301 | 8.0 | Δε (20° C., 1 kHz) = | −3.0 |
| CCH-303 | 5.0 | $k_1$ (20° C.) = | 15.0 pN |
| CC-5-V | 20.0 | $k_3/k_1$ (20° C.) = | 1.08 |
| PCH-53 | 5.0 | | |
| Σ | 100.0 | $V_0$ (20° C.) = | 2.45 V |

These comparative examples represent optimized liquid-crystal media which have good applicational properties and the lowest possible $ε_∥$. The types of compounds used and their concentrations were varied to the extent as allowed in order to achieve the applicational properties. Thus, the $ε_∥$ value of these mixtures is to be regarded as a limit to the values achieved hitherto.

Example M 4

The composition of a mixture of similar composition and similar properties as that of Example 3 is indicated below.

| Compound/abbreviation | Concentration/% by weight | Physical properties | |
|---|---|---|---|
| CCP-302FF | 11.0 | Clearing point (N;I) = | 82.6° C. |
| CCP-502FF | 11.0 | (S,N) transition < | −30° C. |
| CCP-21FF | 7.0 | $n_e$ (20° C., 589 nm) = | 1.5528 |
| CCP-31FF | 7.0 | Δn (20° C., 589 nm) = | 0.0717 |
| PCH-304FF | 5.0 | $ε_{11}$ (20° C., 1 kHz) = | 2.9 |
| PCH-504FF | 5.0 | Δε (20° C., 1 kHz) = | −2.4 |
| CCH-301 | 11.0 | | |
| CCH-5301 | 5.0 | $V_0$ (20° C.) = | 2.58 V |
| PCH-53 | 10.0 | | |
| CH-33 | 2.0 | | |
| CH-35 | 2.0 | | |
| CH-43 | 2.0 | | |
| CH-45 | 2.0 | | |
| CCH-34 | 5.0 | | |
| CCH-35 | 5.0 | | |
| CP-30FF | 5.0 | | |
| CCcB-3-H | 5.0 | | |
| Σ | 100.0 | | |

The liquid-crystal medium has excellent applicational properties and is distinguished by a low $ε_∥$.

Example M 5

| Compound/abbreviation | Concentration/% by weight | Physical properties | |
|---|---|---|---|
| PCH-304FF | 14.0 | Clearing point (N;I) = | 68.0° C. |
| PCH-502FF | 11.0 | $n_e$ (20° C., 589 nm) = | 1.5865 |
| PCH-504FF | 12.0 | Δn (20° C., 589 nm) = | 0.0908 |
| CCP-302FF | 5.0 | $ε_∥$(20° C., 1 kHz) = | 3.9 |
| CCP-502FF | 5.0 | Δε (20° C., 1 kHz) = | −4.7 |
| CC-3-V1 | 17.0 | $k_1$ (20° C.) = | 13.6 pN |
| CCH-35 | 6.0 | $k_3/k1$ = | 1.03 |
| CPY-2-O2 | 10.0 | | |
| CPY-3-O2 | 10.0 | $V_0$ (20° C.) = | 1.83 V |
| CCcB-3-H | 5.0 | | |
| Σ | 100.0 | | |

The liquid-crystal medium has excellent applicational properties and is distinguished by a low threshold and a relatively low $ε_∥$.

What is claimed is:

1. A compound of formula I

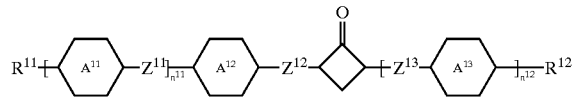

wherein $R^{11}$ and $R^{12}$ are each independently, H, an alkyl group having 1 to 15 carbon atoms which is monosubstituted by CN or $CF_3$ or at least monosubstituted by halogen, in which at least one $CH_2$ group is optionally independently replaced by —O—, —S—, —CH=CH—,

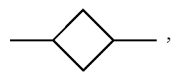

—CO—, —CO—O—, —O—CO— or —O—CO—O— in such a way that O atoms are not linked directly to one another, $Z^{11}$, $Z^{12}$ and $Z^{13}$ are each independently, —$CH_2$—$CH_2$—, —CH=CH—, —C≡O—, —COO—, —OCO—, —$CH_2$O—, —O$CH_2$—, —$CF_2$O—, —O$CF_2$—, —($CH_2$)$_4$—, —CF=CF—, —CH=CF—, —CF=CH— or a single bond,

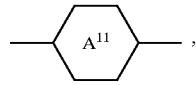

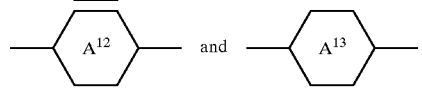

are each independently, (a) trans-1,4-cyclohexylene, in which, one or two non-adjacent $CH_2$ groups are optionally independently replaced by —O— or —S—, (b) 1,4-cyclohexenylene, (c) 1,4-phenylene, in which, one or two OH groups are optionally replaced by N, or
(d) 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, whereby in any of rings (a) to (d) at least one hydrogen atom bound to a carbon atom is optionally replaced by a fluorine atom, and $n^{11}$ and $n^{12}$ are each 0, 1 or 2, and
$n^{11}+n^{12}$ is 1, 2 or 3, with the provisos that $Z^{12}$ is not a single bond and/or $n^{12}$ is 1 or 2.

2. A compound of formula I according to claim 1, wherein $Z^{11}$, $Z^{12}$ and $Z^{13}$ are each single bonds.

3. A compound according to claim 1, of the formulae I1 to I21:

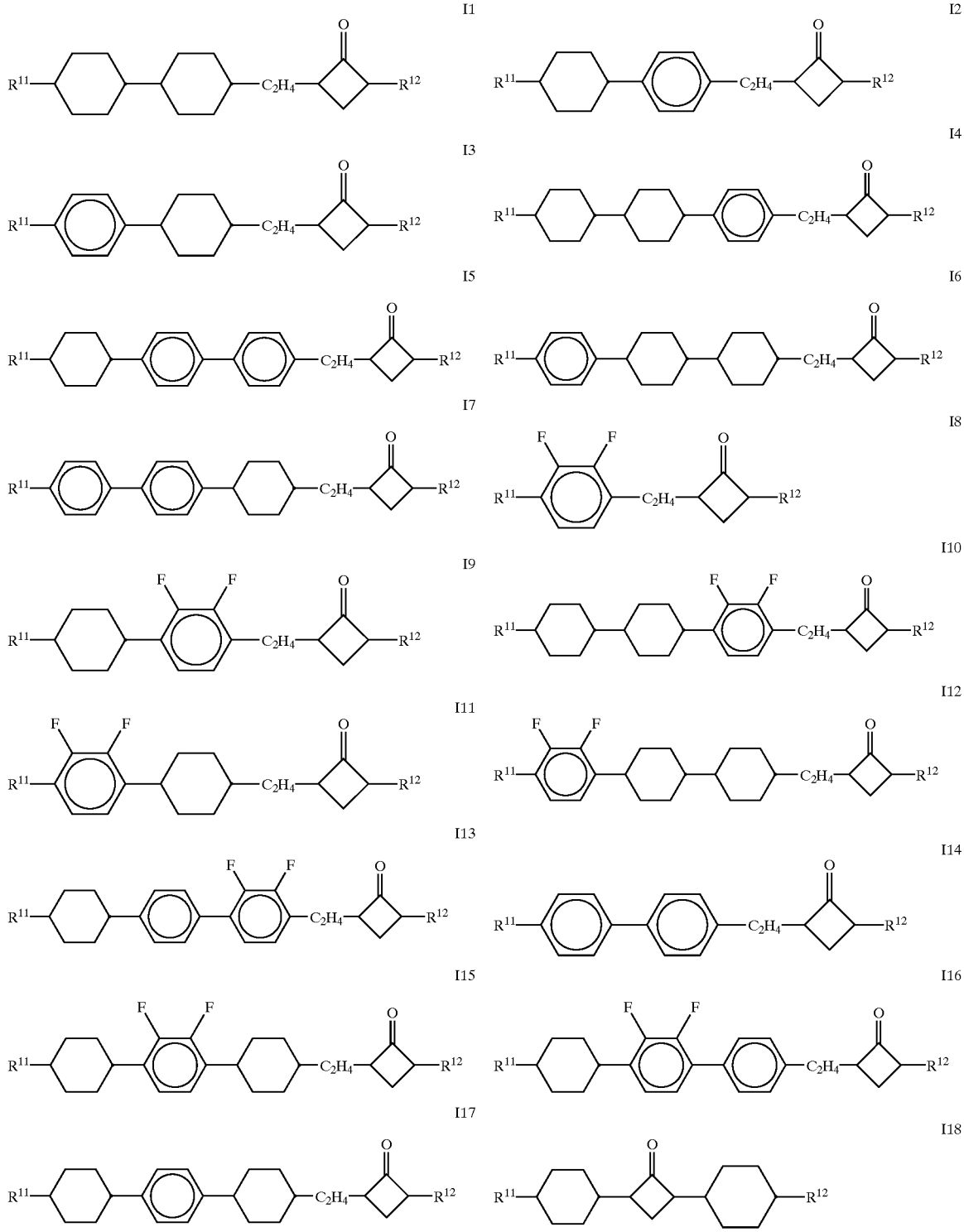

-continued

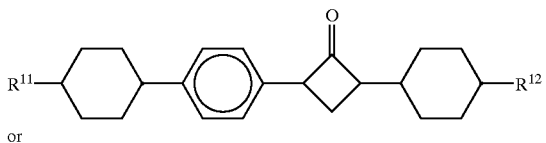
I19

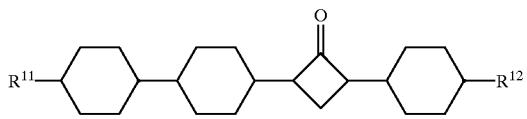
I20 or

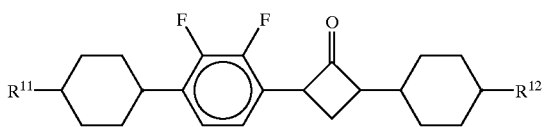

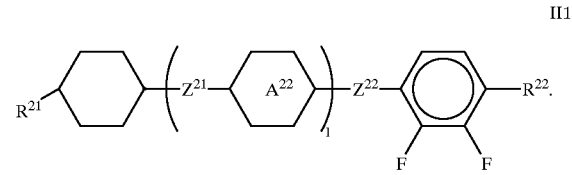
I21

4. A nematic liquid-crystal medium, comprising at least one compound of formula I

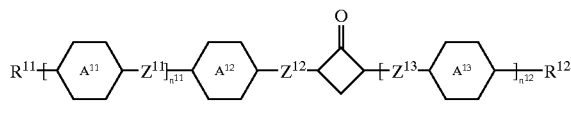
I wherein
$R^{11}$ and $R^{12}$ are each independently, H, an alkyl group having 1 to 15 carbon atoms which is monosubstituted by CN or $CF_3$ or at least monosubstituted by halogen, in which at least one or more $CH_2$ group is optionally, independently replaced by —O—, —S—, —CH=CH—,

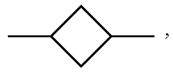,

—CO—, —CO—O—, —O—CO— or —O—CO—O— in such a way that O atoms are not linked directly to one another,
$Z^{11}$, $Z^{12}$ and $Z^{13}$ are each independently, —$CH_2$—$CH_2$—, —CH=CH—, —C≡C—, —COO—, —OCO—, —$CH_2O$—, —$OCH_2$—, —$CF_2O$—, —$OCF_2$—, —$(CH_2)_4$—, —CF=CF—, —CH=CF—, —CF=CH— or a single bond,

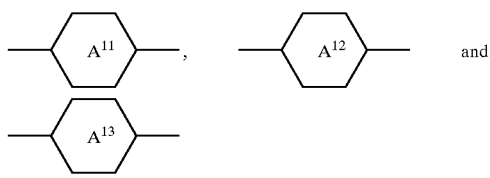

are each independently,
(e) trans-1,4-cyclohexylene, in which one or two non-adjacent $CH_2$ groups are optionally independently replaced by —O— or —S—,
(f) 1,4-cyclohexenylene,
(g) 1,4-phenylene, in which one or two OH groups are optionally replaced by N, or
(h) 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl,
whereby in any of rings (e) to (h) at least one hydrogen atom bound to a carbon atom may be replaced by a fluorine atom and $n^{11}$ and $n^{12}$ are each 0, 1 or 2, and
$n^{11}+n^{12}$ is 1, 2 or 3,
and at least one compound of formula II1

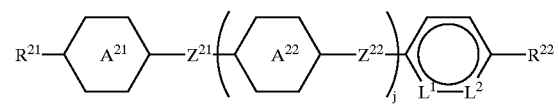
II1 wherein
$R^{21}$ and $R^{22}$ are each independently, as defined for $R^{11}$ in formula I,
$Z^{21}$ and $Z^{22}$ are each independently, as defined for $Z^{11}$ in formula I,

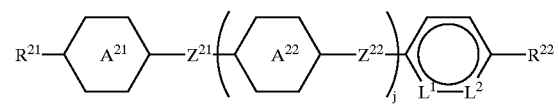 is selected from the groups consisting of and
l is 0 or 1.
5. A liquid-crystal medium comprising at least one compound of formula I according to claim 1.
6. A liquid-crystal medium according to claim 5, further comprising at least one dielectrically negative compound of formula II

II wherein
R²¹ and R²² are each independently as defined for R¹¹ in formula I,
Z²¹ and Z²² are each independently, as defined for Z¹¹ in formula I,

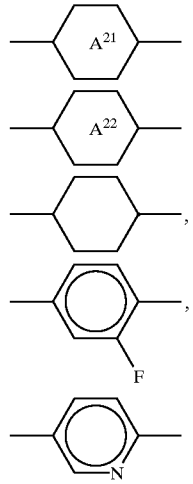 and 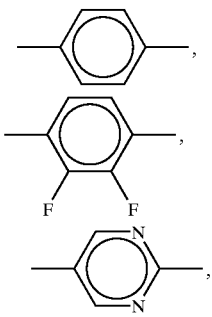 are each independently

L¹ and L² are both C—F or one is N and the other is C—F, and
l is 0 or 1.

7. A liquid-crystal medium according to claim 6, comprising at least one compound of formula II1

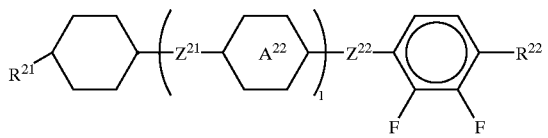

II1

8. A liquid-crystal medium, comprising at least one compound of formula I

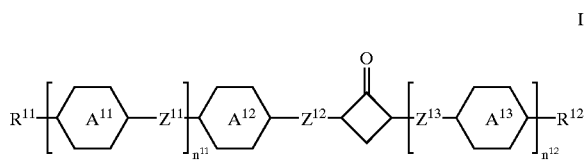

I wherein
R¹¹ and R¹² are each independently, H, an alkyl group having 1 to 15 carbon atoms which is monosubstituted by CN or CF₃ or at least monosubstituted by halogen, in which at least one or more CH₂ group is optionally, independently replaced by —O—, —S—, —CH=CH—,

,

—CO—, —CO—O—, —O—CO— or —O—CO—O— in such a way that O atoms are not linked directly to one another,
$Z^{11}$, $Z^{12}$ and $Z^{13}$ are each independently, —CH₂—CH₂—, —CH=CH—, —C≡C—, —COO—, —OCO—, —CH₂O—, —OCH₂—, —CF₂O—, —OCF₂—, —(CH₂)₄—, —CF=CF—, —CH=CF—, —CF=CH— or a single bond,

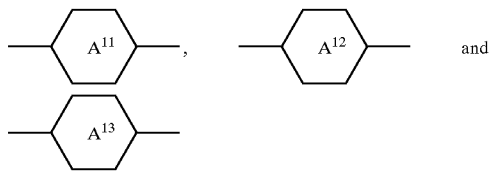 and are each independently,
(i) trans-1,4-cyclohexylene, in which one or two non-adjacent CH₂ groups are optionally independently replaced by —O— or —S—,
(j) 1,4-cyclohexenylene,
(k) 1,4-phenylene, in which one or two CH groups are optionally replaced by N, or
(l) 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl,
whereby in any of rings (e) to (h) at least one hydrogen atom bound to a carbon atom may be replaced by a fluorine atom, and
$n^{11}$ and $n^{12}$ are each 0, 1 or 2, and
$n^{11}+n^{12}$ is 1, 2 or 3,
with the provisos that $Z^{12}$ is not a single bond and/or $n^{12}$ is 1 or 2, and if $n^{11}$ is 0, $Z^{13}$ is not a single bond.

9. An electro-optical display comprising a liquid-crystal medium according to claim 4.
10. An electro-optical display comprising a liquid-crystal medium according to claim 5.
11. An electro-optical display comprising a liquid-crystal medium according to claim 8.
12. A display according to claim 9, which is a VAN LCD.
13. A display according to claim 10, which is a VAN LCD.
14. A display according to claim 11, which is a VAN LCD.
15. A compound of formula I

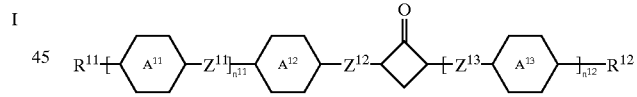

I wherein
R¹¹ and R¹² are each independently, H, an alkyl group having 1 to 15 carbon atoms which is monosubstituted by CN or CF₃ or at least monosubstituted by halogen, in which at least one CH₂ group is optionally independently replaced by —O—, —S—, —CH=CH—,

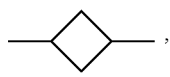,

—CO—, —CO—O—, —O—CO— or —O—CO—O—in such a way that O atoms are not linked directly to one another,
$Z^{11}$, $Z^{12}$ and $Z^{13}$ are each independently, —CH₂—CH₂—, —CH=CH—, —C≡C—, —COO—, —OCO—, —CH₂O—, —OCH₂—, —CF₂O—, —OCF₂—, —(CH₂)₄—, —CF=CF—, —CH=CF—, —CF=CH— or a single bond,

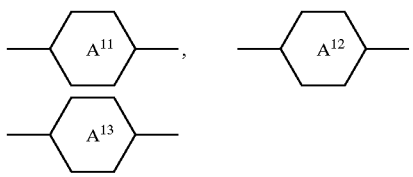

are each independently,
- (m) trans-1,4-cyclohexylene, in which, one or two non-adjacent CH$_2$ groups are optionally independently replaced by —O— or —S—,
- (n) 1,4-cyclohexenylene,
- (o) 1,4-phenylene, in which, one or two CH groups are optionally replaced by N, or
- (p) 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, whereby in any of rings (a) to (d) at least one hydrogen atom bound to a carbon atom is optionally replaced by a fluorine atom, and $n^{11}$ and $n^{12}$ are each 0, 1 or 2, and $n^{11}+n^{12}$ is 1, 2 or 3, with the provisos that $Z^{12}$ is not a single bond and/or $n^{12}$ is 1 or 2, and if $n^{11}$ is 0, $Z^{13}$ is not a single bond.

* * * * *

UNITED STATES PATENT AND TRADEMARK OFFICE
CERTIFICATE OF CORRECTION

PATENT NO. : 6,641,871 B2
DATED : November 4, 2003
INVENTOR(S) : Marcus Reuter et al.

It is certified that error appears in the above-identified patent and that said Letters Patent is hereby corrected as shown below:

Column 51,
Line 1, reads "(OH)" should read -- CH --
Line 60, reads "OH" should read -- CH --

Signed and Sealed this

Twenty-eighth Day of September, 2004

JON W. DUDAS
*Director of the United States Patent and Trademark Office*